United States Patent
Bellenie et al.

(10) Patent No.: US 9,862,711 B2
(45) Date of Patent: Jan. 9, 2018

(54) PYRAZINE DERIVATIVES AS PHOSPHATIDYLINOSITOL 3-KINASE INHIBITORS

(71) Applicants: Benjamin Richard Bellenie, Horsham (GB); Ian Bruce, Tyne and Wear (GB); Andrew James Culshaw, Greenford (GB); Gregory John Hollingworth, Kent (GB); James Neef, Cambridge, MA (US); Matthew Spendiff, Horsham (GB); Simon James Watson, Horsham (GB)

(72) Inventors: Benjamin Richard Bellenie, Horsham (GB); Ian Bruce, Tyne and Wear (GB); Andrew James Culshaw, Greenford (GB); Gregory John Hollingworth, Kent (GB); James Neef, Cambridge, MA (US); Matthew Spendiff, Horsham (GB); Simon James Watson, Horsham (GB)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/303,890

(22) PCT Filed: Apr. 24, 2014

(86) PCT No.: PCT/IB2014/060991
§ 371 (c)(1),
(2) Date: Oct. 13, 2016

(87) PCT Pub. No.: WO2015/162461
PCT Pub. Date: Oct. 29, 2015

(65) Prior Publication Data
US 2017/0029414 A1 Feb. 2, 2017

(51) Int. Cl.
| | | |
|---|---|---|
| *C07D 417/04* | (2006.01) | |
| *C07D 401/04* | (2006.01) | |
| *C07D 403/04* | (2006.01) | |
| *C07D 409/04* | (2006.01) | |
| *C07D 405/14* | (2006.01) | |
| *C07D 403/14* | (2006.01) | |
| *A61K 31/5377* | (2006.01) | |
| *A61K 31/497* | (2006.01) | |

(52) U.S. Cl.
CPC .......... *C07D 417/04* (2013.01); *A61K 31/497* (2013.01); *A61K 31/5377* (2013.01); *C07D 401/04* (2013.01); *C07D 403/04* (2013.01); *C07D 403/14* (2013.01); *C07D 405/14* (2013.01); *C07D 409/04* (2013.01)

(58) Field of Classification Search
CPC .. C07D 417/04; C07D 401/04; C07D 403/04; C07D 403/14; C07D 405/14; C07D 409/04; A61K 31/5377; A61K 31/497
See application file for complete search history.

(56) References Cited

U.S. PATENT DOCUMENTS

| | | |
|---|---|---|
| 2009/0118305 A1 | 5/2009 | Barlaam et al. |
| 2009/0239847 A1 | 9/2009 | Bruce et al. |
| 2012/0071662 A1 | 3/2012 | Sander et al. |

FOREIGN PATENT DOCUMENTS

| | | |
|---|---|---|
| WO | WO2003077918 A1 | 9/2003 |
| WO | WO2003093297 A2 | 11/2003 |
| WO | WO2006124874 A2 | 11/2006 |
| WO | WO2007110337 A1 | 10/2007 |
| WO | WO2007111904 A2 | 10/2007 |
| WO | WO2008006583 A1 | 1/2008 |
| WO | WO2008025820 A1 | 3/2008 |
| WO | WO2009007390 A2 | 1/2009 |
| WO | WO2009013348 A2 | 1/2009 |
| WO | WO2009053737 A2 | 4/2009 |
| WO | WO2009087212 A2 | 7/2009 |
| WO | WO2010071837 A1 | 6/2010 |
| WO | WO2011086531 A2 | 7/2011 |
| WO | WO2015162456 A1 | 10/2015 |
| WO | WO2015162459 A1 | 10/2015 |

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
International Search Report and Written Opinion for International Application No. PCT/IB2014/060991, dated Jul. 1, 2014 (9 pages).
Leahy et al., "Discovery of a novel series of potent and orally bioavailable phosphoinositide 3-kinase γ inhibitors," J Med Chem. Jun. 14, 2012;55(11):5467-82.

* cited by examiner

*Primary Examiner* — Rebecca L Anderson
(74) *Attorney, Agent, or Firm* — Lian Ouyang

(57) ABSTRACT

The present invention provides compounds of formula (I) which inhibit the activity of PI 3-kinase gamma isoform, which are useful for the treatment of diseases mediated by the activation of PI 3-kinase gamma isoform.

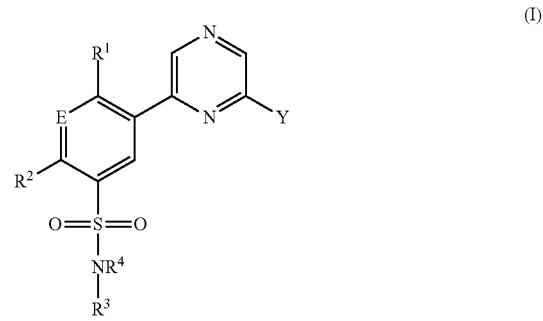

20 Claims, No Drawings

PYRAZINE DERIVATIVES AS PHOSPHATIDYLINOSITOL 3-KINASE INHIBITORS

TECHNICAL FIELD

The present invention relates to novel pyrazinederivatives which are PI 3-kinase gamma isoform selective inhibitors, processes for their preparation, pharmaceutical compositions and medicaments containing them and to their use in diseases and disorders mediated by the activation of PI 3-kinase gamma isoform, particularly asthma.

BACKGROUND

Phosphatidylinositol 3-kinases (PI 3-kinases), a family of enzymes which catalyse the phosphorylation of the 3'-OH of the inositol ring, play a central role in regulating a wide range of cellular processes including metabolism, survival, motility and cell activation (Vanhaesebroeck, B. et al., Annu. Rev. Biochem. 2001, 70, 535). These lipid kinases are divided into 3 major classes, I, II & Ill, according to their structure and in vitro substrate specificity (VVymann, M. et al.; Biochem. Biophys. Acta, 1998, 1436, 127). The most widely understood class I family is further subdivided into subclasses IA and IB. Class IA PI 3-kinases consist of an 85 kDa regulatory/adapter protein and three 110 kDa catalytic subunits (p110α, p110β and p110δ) which are activated in the tyrosine kinase system whilst class IB consists of a single p110γ isoform (PI 3-kinase gamma isoform) which is activated by G protein-coupled receptors. The three members of class II PI 3-kinases (C2α, C2β and C2γ) and single member of class III PI 3 kinases (Vps34) are less well understood. In addition there are also four PI 4-kinases and several PI 3-kinase related protein kinases (termed PIKK's or class IV) including DNA-PK, mTOR, ATM and ATR, all of which have a similar catalytic domain (Abraham R. T. et al.; DNA repair 2004, 3(8-9), 883).

A key role for PI 3-kinase gamma isoform in processes such as leukocyte activation, leukocyte chemotaxis and mast cell degranulation has been shown, thereby generating interest in this target for the treatment of autoimmune and inflammatory disorders (Ghigo et al., Bioessays, 2010, 32, p 185-196; Reif et al., J. Immunol., 2004, 173, p 2236-2240; Laffargue et al., Immunity, 2002, 16, p 441-451; Rommel et al, Nature Rev. Immunology, 2007, 7, p 191; Cushing et al J. Med. Chem., 2012, 55, p 8559; Bergamini et al, Nature Chem. Biol., 2012, 8, p 576). Specifically, numerous publications suggest the potential utility of PI3 Kinase gamma isoform inhibitors for the treatment of asthma (e.g. Thomas et al, Immunology, 2008, 126, p 413; Jiang et al, J. Pharm. Exp. Ther., 2012, 342, p 305; Takeda et al, Int. Arch. Allergy Immunol. 2010, 152 (suppl 1), p 90-95). There are also reports linking inhibition of the PI 3-kinase gamma isoform as having potential therapeutic value in numerous other indications such as cancer (Beagle and Fruman, Cancer Cell, 2011, 19, p 693; Schmid et al, Cancer Cell, 2011, 19, p 715; Xie et al, Biochem. Pharm., 2013, 85, p 1454; Subramaniam et al, Cancer Cell, 2012, 21, p 459), diabetes (Kobayashi et al, Proc. Nat. Acad. Sci, 2011, 108, p 5753; Azzi et al, Diabetes, 2012, 61, p 1509), cardiovascular disease (Fougerat et al, Clin. Sci., 2009, 116, p 791; Fougerat et al, Circulation, 2008, 117, p 1310; Chang et al, Proc. Nat. Acad. Sci., 2007, 104, p 8077; Fougerat et al, Br. J. Pharm., 2012, 166, p 1643), obesity (Becattini et al, Proc. Nat. Acad. Sci., 2011, 108, pE854), Alzheimer's disease (Passos et al, Brain, Behaviour and Immunity, 2010, 24, 493) and pancreatitis (Lupia et al, Am. J. Path, 2004, 165, p 2003). A recent review of PI 3-Kinase isoforms as drug targets is given in Blajecka et al, Current Drug Targets, 2011, 12, p 1056-1081.

WO2009/115517 (Novartis) describes amino pyrazine and pyridine derivatives as PI 3-kinase inhibitors.

WO2009/013348 (Novartis) describes amino pyrimidine derivatives as PI 3-kinase inhibitors.

WO2003/093297 (Exelixis) describes protein kinase modulators and methods of use of such modulators.

Leahy et al., J. Med. Chem., 2012, 55 (11), pp 5467-5482, describe PI 3-kinase gamma isoform inhibitors.

Hence, there is a need for potent, selective inhibitors of PI 3-kinase gamma isoform.

DESCRIPTION OF THE EMBODIMENTS

In an embodiment 1 of the invention, there is provided a compound of formula (I)

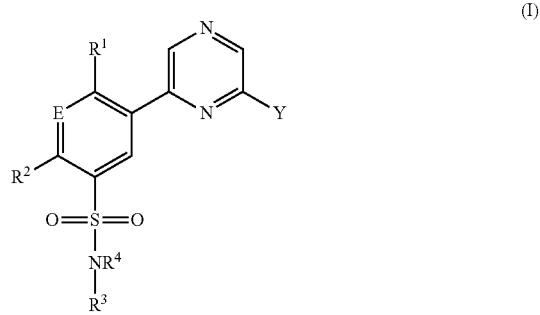

wherein
E is selected from N and $CR^E$;
$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;
$R^3$ is selected from
(i) $C_{1-4}$ alkyl which is unsubstituted or substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(ii) $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(iii) —$C_{3-6}$ cycloalkyl or —O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;
(iv) —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(v) —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

(vi) —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

$R^4$ is selected from H and $C_{1-4}$ alkyl; or $R^3$ and $R^4$ together with the nitrogen atom to which they are attached form a $C_{3-6}$ heterocyclyl, which $C_{3-6}$ heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —($C_{0-3}$ alkyl)-$NR^{3a}R^{3b}$, —($C_{0-3}$ alkyl)-$C_{3-6}$ cycloalkyl and —($C_{0-3}$ alkyl)-$C_{3-6}$ heterocyclyl;

or a pharmaceutically acceptable salt thereof.

Definitions

"Halo" or "halogen", as used herein, may be fluoro, chloro, bromo or iodo.

"$C_{1-4}$ alkyl", as used herein, denotes straight chain or branched alkyl having 1-4 carbon atoms. If a different number of carbon atoms is specified, such as $C_6$ or $C_3$, then the definition is to be amended accordingly, such as "$C_1$-$C_4$ alkyl" will represent methyl, ethyl, propyl, isopropyl, butyl, isobutyl, sec-butyl and tert-butyl.

"$C_{1-4}$ alkoxy", as used herein, refers to an —O—$C_{1-4}$ alkyl group wherein $C_{1-4}$ alkyl is as defined herein. Examples of such groups include methoxy, ethoxy, propoxy, butoxy, pentoxy or hexoxy and the like. As for alkyl unless a particular structure is specified the terms propoxy, butoxy etc include all straight and branched chain forms having the appropriate number of carbon atoms e.g. propoxy includes n-propoxy and isopropoxy.

"$C_{1-4}$ haloalkoxy" as used herein refers to an —O—$C_{1-4}$ alkyl group wherein $C_{1-4}$ alkyl is as defined herein and substituted with one or more halogen groups, e.g. —O—$CF_3$.

"$C_{1-4}$ haloalkyl", as used herein, denotes straight chain or branched alkyl having 1-4 carbon atoms with at least one hydrogen substituted with a halogen. If a different number of carbon atoms is specified, such as $C_6$ or $C_3$, then the definition is to be amended accordingly, such as "$C_1$-$C_4$-Haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_{3-6}$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, then the definition is to be amended accordingly.

The term "hydroxy" or "hydroxyl" refers to —OH.

"$C_{1-4}$ hydroxyalkyl", as used herein, denotes a straight chain or branched alkyl having 1-4 carbon atoms with at least one hydrogen substituted with a hydroxy group. If a different number of carbon atoms is specified, such as $C_6$ or $C_3$, then the definition is to be amended accordingly, such as "$C_1$-$C_4$ hydroxyalkyl" will represent methyl, ethyl, propyl, isopropyl, butyl, isobutyl, sec-butyl and tert-butyl that have at least one hydrogen substituted with hydroxy.

"$C_{3-6}$ heterocyclyl ring" refers to a 3 to 6 membered saturated or partially unsaturated aliphatic ring system which contains 1 to 3 heteroatoms selected from oxygen and nitrogen. Suitable examples of such ring systems include pyrrolidinyl, piperidinyl, piperazinyl, morpholinyl, tetrahydrofuranyl, tetrahydropyranyl, pyrrolinyl, or oxazolinyl.

"5-6 membered heteroaryl" refers to a 5-6 membered aromatic ring system which contains 1 to 3 heteroatoms selected from oxygen, nitrogen or sulphur. Examples of 5-membered heteroaryl rings in this instance include furanyl, pyrrolyl, oxazolyl, thiazolyl, imidazolyl, oxadiazolyl, thiadiazolyl, triazolyl, isothiazolyl, isoxazolyl, thiophenyl, or pyrazolyl. Examples of 6-membered heteroaryl rings include pyridinyl, pyridazinyl, pyrimidinyl, pyrazinyl, or triazinyl.

"Oxo" refers to =O.

The term "a," "an," "the" and similar terms used in the context of the present invention (especially in the context of the claims) are to be construed to cover both the singular and plural unless otherwise indicated herein or clearly contradicted by the context.

The term "treatment" as used herein refers to both to symptomatic and prophylactic treatment, particularly symptomatic.

Various embodiments of the invention are described herein. It will be recognized that features specified in each embodiment may be combined with other specified features to provide further embodiments.

In an embodiment 2 of the invention, there is provided a compound of formula (I), wherein E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;

$R^3$ is selected from (i) $C_{1-4}$ alkyl which is substituted with 1 to 3 substituents independently selected from hydroxy, $C_{1-4}$ hydroxyalkyl, halogen, $C_{1-4}$ haloalkyl, $C_{1-4}$alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

(ii) $C_{1-4}$ alkoxy which is substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

(iii) —$C_{3-6}$ cycloalkyl or —O—$C_{3-6}$ cycloalkyl wherein the $C_{3-6}$ cycloalkyl is substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(iv) a —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the second $C_{3-6}$ cycloalkyl or $C_{3-6}$ heterocyclyl is substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;

(v) a —($C_{0-3}$ alkyl)-$C_{36}$ heterocyclyl or —(O—$C_{0-3}$ alkyl)-$C_{36}$ heterocyclyl wherein the $C_{3-6}$ heterocyclyl contains at least one heteroatom selected from O and N, and wherein said $C_{3-6}$ heterocyclyl is substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

(vi) a —($C_{0-3}$ alkyl)-$C_{36}$ heterocyclyl or —(O—$C_{0-3}$ alkyl)-$C_{36}$ heterocyclyl wherein the $C_{3-6}$ heterocyclyl contains at least one heteroatom selected from O and N, and wherein said $C_{3-6}$ heterocyclyl is fused to a second $C_{3-6}$ heterocyclyl or a $C_{3-6}$ cycloalkyl by one single carbon atom, and wherein said second $C_{3-6}$ heterocyclyl or $C_{3-6}$ cycloalkyl is substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;

$R^{3a}$ and $R^{3b}$ are independently selected from H, $C_{1-4}$ alkyl and $C_{1-4}$ haloalkyl;

$R^4$ is selected from H and $C_{1-4}$ alkyl; or $R^3$ and $R^4$ together with the nitrogen atom to which they are attached form a $C_{3-6}$ heterocyclyl, which $C_{3-6}$ heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl;

Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —($C_{0-3}$ alkyl)-$NR^{3a}R^{3b}$, —($C_{0-3}$ alkyl)-$C_{3-6}$ cycloalkyl and —($C_{0-3}$ alkyl)-$C_{3-6}$ heterocyclyl;

or a pharmaceutically acceptable salt thereof.

In an embodiment 3 of the invention, there is provided a compound or salt according to embodiment 1 or 2 wherein E is $CR^E$ and $R^E$ is H.

In an embodiment 4 of the invention, there is provided a compound or salt according to any one of embodiments 1 to 3 wherein $R^1$ is selected from $C_{1-4}$ alkyl and H.

In an embodiment 5 of the invention, there is provided a compound or salt according to embodiment 4, wherein $R^1$ is selected from methyl and H, particularly methyl.

In an embodiment 6 of the invention, there is provided a compound or salt according to any one of embodiments 1 to 5, wherein $R^2$ is selected from H, $C_{1-4}$ alkyl and halogen.

In an embodiment 7 of the invention, there is provided a compound or salt according to embodiment 6, wherein $R^2$ is selected from H, fluoro, chloro and methyl, particularly H and fluoro, more particularly H.

In an embodiment 8 of the invention, there is provided a compound or salt according to any one of embodiments 1 to 7, wherein $R^3$ is selected from (i) $C_{1-4}$ alkyl substituted with 1 to 3 substituents independently selected from hydroxy, $C_{1-4}$ alkyl, halogen, oxo, and —$NR^{3a}R^{3b}$;

(ii) $C_{1-4}$ alkoxy substituted with 1 to 3 substituents independently selected from hydroxy, halogen and $C_{1-4}$ alkyl;

(iii) alkyl)-$C_{3-6}$ cycloalkyl wherein the $C_{3-6}$ cycloalkyl is substituted with 1 to 3 substituents independently selected from hydroxy, $C_{1-4}$ hydroxyalkyl and halogen;

(iv) —($C_{0-3}$ alkyl)-$C_{3-6}$ cycloalkyl spiro fused to a second $C_{3-6}$ cycloalkyl by one single carbon atom, wherein the second $C_{3-6}$ cycloalkyl is substituted with 1 to 3 substituents independently selected from hydroxy and halogen; and (v) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl;

(vi) a —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, hydroxy and $C_{1-4}$ hydroxyalkyl;

$R^{3a}$ and $R^{3b}$ are independently selected from H and $C_{1-4}$ alkyl;

$R^4$ is selected from H and $C_{1-4}$alkyl; or $R^3$ and $R^4$ together with the nitrogen atom to which they are attached form a $C_{3-6}$ heterocyclyl, which $C_{3-6}$ heterocyclyl is unsubstituted or substituted with 1 to 3 substituents independently selected from hydroxy, $C_{1-4}$ hydroxyalkyl and $C_{1-4}$ alkyl.

In an embodiment 9 of the invention, there is provided a compound or salt according to any one of embodiments 1 to 7, wherein $R^3$ is $C_{1-4}$ alkyl which is unsubstituted or substituted with 1 to 3 substituents independently selected from hydroxy, $C_{1-4}$ hydroxyalkyl, halogen, $C_{1-4}$ haloalkyl, $C_{1-4}$ alkoxy, $C_{1-4}$ alkyl, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl.

In an embodiment 10 of the invention, there is provided a compound or salt according to embodiment 9, wherein $R^3$ is selected from propyl, butyl and pentyl substituted with 1 to 3 substituents independently selected from hydroxy, $C_{1-4}$ alkyl, halogen, —$NR^{3a}R^{3b}$ and oxo.

In an embodiment 11 of the invention, there is provided a compound or salt according to embodiment 9, wherein $R^3$ is selected from 3-hydroxypropyl-;
3-hydroxy-2,2-dimethylpropyl-;
3-hydroxy-3-methylbutyl-;
2-hydroxy-2-methylpropyl-;
4,4,4-trifluoro-3-hydroxybutyl-;
2,2-difluoroethyl-;
3,3-dimethyl-2-oxo-butyl; and
3,3,3-trifluoro-2-hydroxy-2-methylpropyl-.

In an embodiment 12 of the invention, there is provided a compound or salt according to embodiment 11, wherein $R^3$ is selected from
3-hydroxypropyl-;
3-hydroxy-2,2-dimethylpropyl-;
2-hydroxy-2-methylpropyl; and
3-hydroxy-3-methylbutyl-.

In an embodiment 13 of the invention, there is provided a compound or salt according to any one of embodiments 1 to 7, wherein $R^3$ is $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;

In an embodiment 14 of the invention, there is provided a compound or salt according to any one of embodiment 13, wherein $R^3$ is selected from propoxy, butoxy and pentoxy substituted with 1 to 3 substituents selected from hydroxy, $C_{1-4}$ alkyl and halogen.

In an embodiment 15 of the invention, there is provided a compound or salt according to any one of embodiment 14, wherein $R^3$ is 2-hydroxy-2-methylpropoxy-.

In an embodiment 16 of the invention, there is provided a compound or salt according to any one of embodiments 1 to 7, wherein $R^3$ is —$C_{3-6}$ cycloalkyl or —O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —$(C_{0-3}$ alkyl)-$NR^{3a}R^{3b}$.

In an embodiment 17 of the invention, there is provided a compound or salt according to embodiment 16, wherein $R^3$ is selected from —$(C_{0-3}$ alkyl)-cyclohexyl, —$(C_{0-3}$ alkyl)-cyclobutyl and —$(C_{0-3}$ alkyl)-cyclopropyl, and wherein the cyclohexyl, cyclobutyl and cyclopropyl are substituted with 1 or 2 substituents independently selected from hydroxy, $C_{1-4}$ hydroxyalkyl and halogen.

In an embodiment 18 of the invention, there is provided a compound or salt according to embodiment 17, wherein $R^3$ is selected from
4-hydroxycyclohexyl-;
3-hydroxycyclobutyl-methyl-;
1-hydroxycyclobutyl-methyl-;
1-(hydroxymethyl)cyclopropyl; and
1-hydroxycyclopropyl-methyl-.

In an embodiment 19 of the invention, there is provided a compound or salt according to embodiment 17, wherein $R^3$ is selected from
4-hydroxycyclohexyl- and
3-hydroxycyclobutyl-methyl-.

In an embodiment 20 of the invention, there is provided a compound or salt according to any one of embodiments 1 to 7, wherein $R^3$ is —$(C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —$(C_{0-3}$ alkyl)-$NR^{3a}R^{3b}$.

In an embodiment 21 of the invention, there is provided a compound or salt according to embodiment 20, wherein $R^3$ is selected from spiro[3.3]heptan-2-yl, spiro[3.4]octan-6-yl, spiro[4.4]nonan-2-yl and spiro[3.4]undecan-3-yl, which is substituted by 1 to 3 substituents selected from hydroxy and halogen.

In an embodiment 22 of the invention, there is provided a compound or salt according to embodiment 21, wherein $R^3$ is 6-hydroxyspiro[3.3]heptan-2-yl.

In an embodiment 23 of the invention, there is provided a compound or salt according to any one of embodiments 1 to 7, wherein $R^3$ is —$(C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl;
or —$(C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —$(C_{0-3}$ alkyl)-$NR^{3a}R^{3b}$.

In an embodiment 24 of the invention, there is provided a compound or salt according to embodiment 23, wherein $R^3$ is selected from a —$(C_{0-3}$ alkyl)-tetrahydrofuranyl, alkyl)-oxetanyl, alkyl)-pyrrolidinyl, and —$(C_{0-3}$ alkyl)-tetrahydropyranyl, each of which is unsubstituted or substituted with 1 to 3 substituents independently selected from hydroxy, $C_{1-4}$ alkyl and $C_{1-4}$ hydroxyalkyl.

In an embodiment 25 of the invention, there is provided a compound or salt according to embodiment 24, wherein $R^3$ is selected from
(1-ethylpyrrolidin-2-yl)methyl,
(tetrahydro-2H-pyran-4-yl),
(3-hydroxyoxetan-3-yl)methyl,
(3-methyloxetan-3-yl)methyl,
(4-hydroxy-tetrahydropyran)methyl,
(3-hydroxymethyl-oxetan-3-yl)methyl, and
(tetrahydrofuran-3-yl)methyl.

In an embodiment 26 of the invention, there is provided a compound or salt according to any one of embodiment 1 to 25, wherein $R^4$ is H or methyl.

In an embodiment 27 of the invention, there is provided a compound or salt according to any one of embodiment 1 to 7, wherein $R^3$ and $R^4$ together with the nitrogen atom to which they are attached form a $C_{3-6}$ heterocyclyl, which heterocyclyl is unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl.

In an embodiment 28 of the invention, there is provided a compound or salt according to embodiment 27, wherein $R^3$ and $R^4$ together with the nitrogen atom to which they are attached form a piperazinyl, piperidinyl, or azetidinyl, which are unsubstituted or substituted with 1 to 3 substituents independently selected from hydroxy, $C_{1-4}$ hydroxyalkyl and $C_{1-4}$ alkyl.

In an embodiment 29 of the invention, there is provided a compound or salt according to embodiment 28, wherein $R^3$ and $R^4$ together with the nitrogen atom to which they are attached form a
3-(trifluoromethyl)piperazin-1-yl,
3,3-difluoropiperidin-1-yl, or
1-(hydroxymethyl)azetidin-3-yl.

In an embodiment 30 of the invention, there is provided a compound or salt according to any one of embodiment 1 to 29, wherein Y is selected from
thiazolyl,
pyrazolyl,
pyridyl,
triazolyl,
imidazolyl,
oxadiazolyl,
pyrimidinyl,
isoxazolyl, oxazolyl, and
thienyl;
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —$NR^{3a}R^{3b}$, —($C_{0-3}$ alkyl)-$C_{3-6}$ cycloalkyl and —($C_{0-3}$ alkyl)-$C_{3-6}$ heterocyclyl.

In an embodiment 31 of the invention, there is provided a compound or salt according to embodiment 30, wherein Y is selected from
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
imidazol-1-yl,
1,2,4-oxadiazol-5-yl,
1,3,4-oxadiazol-2-yl,
oxazol-5-yl,
isoxazol-5-yl,
pyrimidin-5-yl,
thien-3-yl,
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy and —($C_{0-3}$ alkyl)-$C_{3-6}$ cycloalkyl.

In an embodiment 32 of the invention, there is provided a compound or salt according to embodiment 31, wherein Y is selected from
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
imidazol-1-yl,
1,2,4-oxadiazol-5-yl,
oxazol-5-yl,
isoxazol-5-yl,
pyrimidin-5-yl,
thien-3-yl,
each of which is unsubstituted or substituted with 1 to 3 substituents independently selected from methyl, ethyl, propyl, isopropyl, cyclopropyl, $CF_3$, $CF_3CH_2$—, hydroxyethyl, methoxyethyl and methoxy.

In an embodiment 33 of the invention, there is provided a compound or salt according to embodiment 30, wherein Y is selected from
5-morpholin-4-ylmethyl-thien-3-yl,
3-cyclopropyl-[1,2,4]triazol-1-yl,
2-cyclopropyl-thiazol-5-yl,
2,5-dimethyl-2H-[1,2,3]triazol-4-yl,
2-methylthiazol-5-yl,
1,3-dimethyl-1H-pyrazol-4-yl,
1,2,4-triazol-1-yl,
3-isopropyl-1,2,4-oxadiazol-5-yl,
3-methyl-[1,2,4]oxadiazol-5-yl,
1-methyl-1H-pyrazol-4-yl,
1H-pyrazol-1-yl,
3-ethyl-1,2,4-oxadiazol-5-yl,
2-methyl-2H-1,2,3-triazol-4-yl,
(2,2,2-trifluoro-ethyl)-1H-pyrazol-4-yl
1H-pyrazol-4-yl,
3-methylisoxazol-5-yl,
2-methylpyridin-4-yl)pyrazin-2-yl,
1H-1,2,4-triazol-1-yl,
3-propyl-1,2,4-oxadiazol-5-yl,
2-methyl-oxazol-5-yl,
pyrimidin-5-yl,
3-methyl-1H-1,2,4-triazol-1-yl,
5-methyl-1,3,4-oxadiazol-2-yl,
1-methyl-1H-pyrazol-5-yl,
pyrid-3-yl,
pyrid-4-yl,
2-methyl-pyrid-4-yl,
3-methyl-1,2,4-oxadiazol-5-yl,
2-methylthiazol-4-yl,
4-methyl-1H-imidazol-1-yl,
1-ethyl-1H-pyrazol-4-yl,
3,5-dimethyl-1H-pyrazol-1-yl,
3-cyclopropyl-1,2,4-oxadiazol-5-yl,
3-methylisoxazol-5-yl,
1-isopropyl-1H-pyrazol-4-yl,
1H-1,2,4-triazol-1-yl,
1-propyl-1H-pyrazol-4-yl,
4-methoxypyridin-3-yl,
pyrazol-3-yl,
3-methylisoxazol-5-yl, and
1-(2-methoxyethyl)-1H-pyrazol-4-yl.

In an embodiment 34 of the invention, there is provided a compound or salt according to any one of embodiment 1 to 29, wherein Y is selected from
thiazolyl,
oxadiazolyl,
isoxalolyl,
pyrazolyl,
pyridyl, and
triazolyl,
each of which is unsubstituted or substituted with 1 to 3 substituents independently selected from $C_{1-4}$ alkyl, $C_{1-4}$ haloalkyl, $C_{1-4}$ alkoxy, $C_{1-4}$ haloalkoxy, —($C_{0-3}$ alkyl)-$C_{3-6}$ cycloalkyl and —($C_{0-3}$ alkyl)-$C_{3-6}$ heterocyclyl.

In an embodiment 35 of the invention, there is provided a compound or salt according to embodiment 34, wherein Y is selected from
thiazol-5-yl,
isoxazol-5-yl,
oxadiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
each of which is unsubstituted or substituted with 1 or 2 substituents independently selected from methyl, ethyl, propyl and isopropyl.

In an embodiment 36 of the invention, there is provided a compound according to embodiment 1 selected from
N-(3-Hydroxy-propyl)-4-methyl-3-[6-(2-methyl-thiazol-5-yl)-pyrazin-2-yl]-benzenesulfonamide;
3-[6-(1,3-Dimethyl-1H-pyrazol-4-yl)-pyrazin-2-yl]-N-(2-hydroxy-2-methyl-propyl)-4-methyl-benzenesulfonamide;
3-[6-(1,3-Dimethyl-1H-pyrazol-4-yl)-pyrazin-2-yl]-N-(3-hydroxy-3-methyl-butyl)-4-methyl-benzenesulfonamide;

3-[6-(1,3-Dimethyl-1H-pyrazol-4-yl)-pyrazin-2-yl]-4-methyl-N-(3-methyl-oxetan-3-ylmethyl)-benzenesulfonamide;

Trans-N-(4-Hydroxycyclohexyl)-4-methyl-3-(6-(2-methyl-thiazol-5-yl)pyrazin-2-yl)benzenesulfonamide;

3-[6-(1,3-Dimethyl-1H-pyrazol-4-yl)-pyrazin-2-yl]-N-(6-hydroxy-spiro[3.3]hept-2-yl)-4-methyl-benzenesulfonamide;

Cis 3-[6-(1,3-Dimethyl-1H-pyrazol-4-yl)-pyrazin-2-yl]-N-(3-hydroxy-cyclobutylmethyl)-4-methyl-benzenesulfonamide;

3-[6-(1,3-Dimethyl-1H-pyrazol-4-yl)-pyrazin-2-yl]-N-(3-hydroxy-2,2-dimethyl-propyl)-4-methyl-benzenesulfonamide;

N-(3-Hydroxy-3-methyl-butyl)-4-methyl-3-{6-[1-(2-morpholin-4-yl-ethyl)-1H-pyrazol-4-yl]-pyrazin-2-yl}-benzenesulfonamide;

N-(3-Hydroxy-3-methyl-butyl)-4-methyl-3-{6-[3-methyl-1-(2-morpholin-4-yl-ethyl)-1H-pyrazol-4-yl]-pyrazin-2-yl}-benzenesulfonamide;

Trans N-(4-Hydroxy-cyclohexyl)-4-methyl-3-(6-pyridin-3-yl-pyrazin-2-yl)-benzenesulfonamide;

Trans N-(4-Hydroxy-cyclohexyl)-4-methyl-3-[6-(5-morpholin-4-ylmethyl-thiophen-3-yl)-pyrazin-2-yl]-benzenesulfonamide;

Cis 3-[6-(2,5-Dimethyl-2H-pyrazol-3-yl)-pyrazin-2-yl]-N-(3-hydroxy-cyclobutylmethyl)-4-methyl-benzenesulfonamide;

or a pharmaceutically acceptable salt thereof.

In an embodiment 37 of the invention, there is provided a compound or salt according to any one of embodiments 1-36, or a pharmaceutically acceptable salt thereof, for use in medicine.

In an embodiment 38 of the invention, there is provided a compound or salt according to any one of embodiments 1-36 for use in the treatment of a disorder or disease mediated by the activation of PI 3-kinase gamma isoform (p110-γ).

In an embodiment 39 of the invention, there is provided a compound or salt according to any one of embodiments 1-36 for use in the treatment of inflammatory, obstructive or allergic conditions.

In an embodiment 40 of the invention, there is provided a compound or salt according to any one of embodiments 1-36 for use in the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 41 of the invention, there is provided a compound or salt according to any one of embodiments 1-36 for use in the treatment of respiratory diseases, particularly asthma, COPD, COAD, COLD, chronic bronchitis, dyspnea or emphysema, more particularly asthma.

In an embodiment 42 of the invention, there is provided the use of a compound according to any one of embodiments 1-36, or a pharmaceutically acceptable salt thereof, in the manufacture of a medicament for the treatment of a disorder or disease mediated by the activation of PI 3-kinase gamma isoform (p110-γ).

In an embodiment 43 of the invention, there is provided the use of a compound according to any one of embodiments 1-36, or a pharmaceutically acceptable salt thereof, in the manufacture of a medicament for the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 44 of the invention, there is provided the use of a compound according to any one of embodiments 1-36, or a pharmaceutically acceptable salt thereof, in the manufacture of a medicament for the treatment of respiratory diseases, particularly asthma, COPD, COAD, COLD, chronic bronchitis, dyspnea or emphysema, more particularly asthma.

In an embodiment 45 of the invention, there is provided the use of a compound according to any one of embodiments 1-36, or a pharmaceutically acceptable salt thereof, for the treatment of a disorder or disease mediated by the activation of PI 3-kinase gamma isoform (p110-γ).

In an embodiment 46 of the invention, there is provided the use of a compound according to any one of embodiments 1-36, or a pharmaceutically acceptable salt thereof, for the treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis.

In an embodiment 47 of the invention, there is provided the use of a compound according to any one of embodiments 1-36, or a pharmaceutically acceptable salt thereof, for the treatment of respiratory diseases, particularly asthma, COPD, COAD, COLD, chronic bronchitis, dyspnea or emphysema, more particularly asthma.

In an embodiment 48 of the invention, there is provided a method of treating a disorder or disease mediated by the activation of PI 3-kinase gamma isoform (p110-γ), comprising administering to a subject in need thereof a therapeutically effective amount of a compound according to any one of embodiments 1-36, or a pharmaceutically acceptable salt thereof.

In an embodiment 49 of the invention, there is provided a method of treating respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity and restenosis, comprising administering to a subject in need thereof a therapeutically effective amount of a compound according to any one of embodiments 1-36, or a pharmaceutically acceptable salt thereof.

In an embodiment 50 of the invention, there is provided a method of treating respiratory diseases, particularly asthma, COPD, COAD, COLD, chronic bronchitis, dyspnea or emphysema, more particularly asthma, comprising administering to a subject in need thereof a therapeutically effective amount of a compound according to any one of embodiments 1-36, or a pharmaceutically acceptable salt thereof.

In an embodiment 51 of the invention, there is provided a pharmaceutical composition comprising:
a therapeutically effective amount of the compound according to any one of embodiments 1-36, or a pharmaceutically acceptable salt thereof, and one or more pharmaceutically acceptable carriers.

In an embodiment 52 of the invention, there is provided a pharmaceutical combination, comprising:
a therapeutically effective amount of the compound according to any one of embodiments 1 to 36, or a pharmaceutically acceptable salt thereof, and a second active agent.

In an embodiment 53 of the invention, there is provided a pharmaceutical combination according to embodiment 52, wherein the second active agent is selected from an anti-inflammatory, bronchodilatory or antihistamine drug substance.

In another embodiment, individual compounds according to the invention are those listed in the Examples section below.

The term "compounds of the present invention" or "a compound of the present invention" refers to a compound as defined in any one of embodiments 1-36.

The compounds as defined in embodiments 1-36 may be synthesized by the general synthetic routes below, specific examples of which are described in more detail in the Examples.

Scheme 1

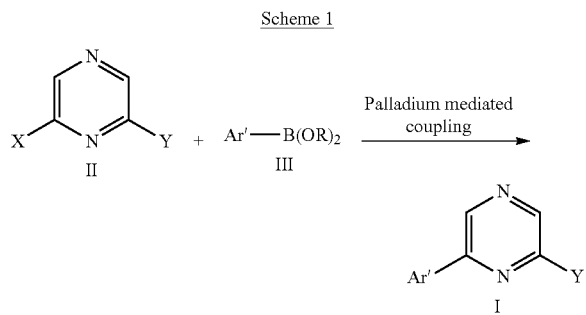

wherein Ar' refers to

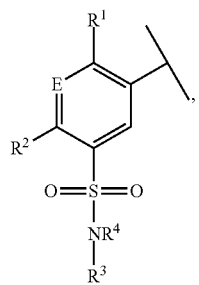

and Y, $R^1$, $R^2$, $R^3$, $R^4$ and E are defined as in embodiment 1, and X is a halogen such as I, Br or Cl.

The reaction between A1 and A2 is carried out using a suitable palladium catalyst, such as Pd(dppf)Cl$_2$, in a suitable solvent, such as DME or MeCN. The reaction typically includes a base, such as sodium carbonate or i-Pr$_2$NEt and may be carried out at elevated temperatures, such as at reflux.

As an alternative to the above scheme, A1 may be reacted with a suitable boron compound in the presence of a catalyst in order to form the boronic acid/boronic anhydride derivative of A1 and then reacted with Ar'—Br (IV) to form a compound of Formula I in a two-step procedure.

Scheme 2

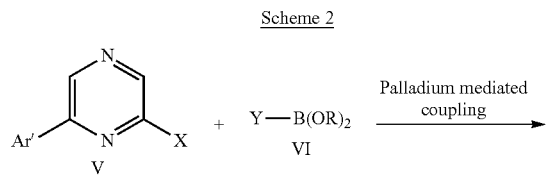

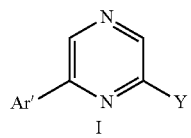

wherein Ar' refers to

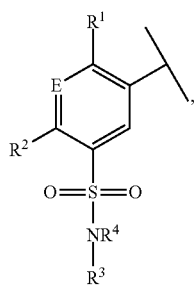

and Y, $R^1$, $R^2$, $R^3$, $R^4$ and E are defined as in embodiment 1, and X is a halogen such as I, Br or Cl.

The reaction between compounds V and VI is carried out using a suitable palladium catalyst, such as Pd(dppf)Cl$_2$, in a suitable solvent, such as DME or MeCN. The reaction typically includes a base, such as sodium carbonate or KOAc and may be carried out at elevated temperatures, such as at reflux.

Scheme 3

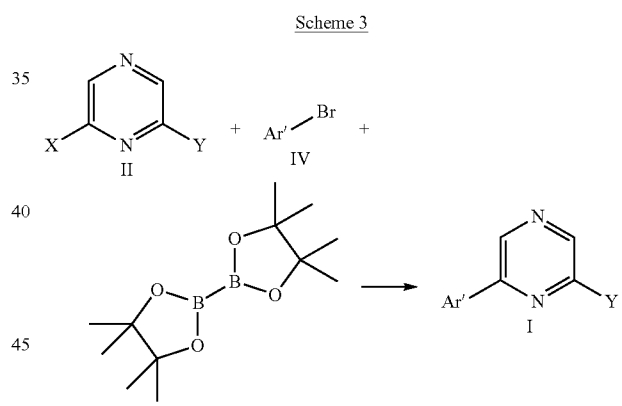

wherein Ar' refers to

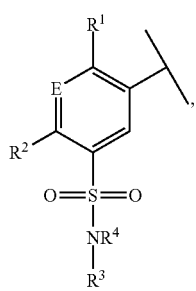

and Y, $R^1$, $R^2$, $R^3$, $R^4$ and E are defined as in embodiment 1, and X is a halogen such as I, Br or Cl. This is a two step, one pot boronylation followed by a Suzuki reaction using typical conditions for both, e.g. Pd catalyst.

Scheme 4

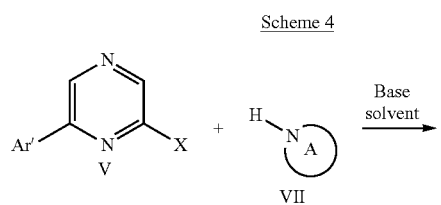

wherein Ar' refers to

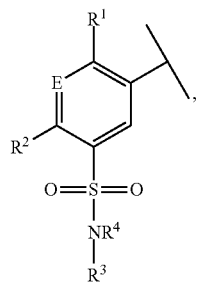

and $R^1$, $R^2$, $R^3$, $R^4$ and E are defined as in embodiment 1, X is a halogen such as I, Br or Cl and A is a 5-6-membered heteroaryl as defined herein.

The reaction is carried out in the presence of a suitable base such as an amine, or an alkali metal hydride or carbonate, e.g. NaH or $CsCO_3$, in a suitable solvent such as dimethyl acetamide (DMA), typically at an elevated temperature of up to 150° C. optionally in the presence of CuI and N,N-dimethylglycine.

Scheme 5

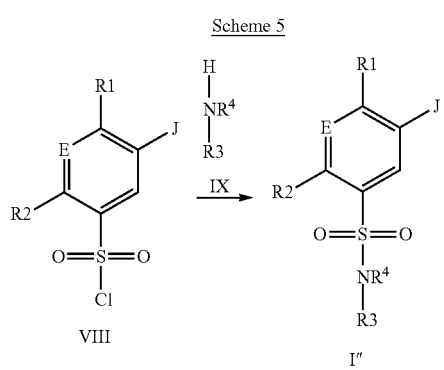

wherein Y, $R^1$, $R^2$, $R^3$, $R^4$ and E are defined as in embodiment 1, and J is bromo or

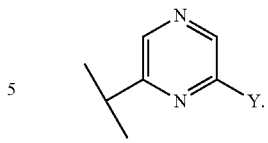

Compound of formula I" may be prepared by reacting VIII with an amine IX in the presence of a suitable base such as pyridine, triethylamine or diisopropylethylamine, in a suitable solvent such as DCM, THF, pyridine or dimethylacetamide, at a suitable temperature such as between 0° C. to room temperature.

Compounds of formula II are commercially available or may be prepared according to known methods. Compound of formula III are commercially available or may be prepared from compounds of formula IV using standard conditions well known to a person skilled in the art (see experimental 'Boronic esters'). Compounds of formula V may be prepared by reacting a compound of formula III with a compound of formula VIII under typical Suzuki reaction conditions (see Scheme 6) or may be prepared by reacting a compound of formula III with a compound of formula IX under typical Suzuki reaction conditions followed by a halogenation (see Scheme 7)

Scheme 6

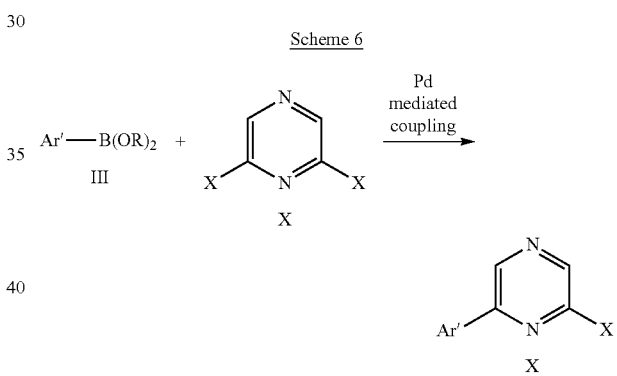

Scheme 7

Compounds of formula VI are commercially available or may be prepared according to known methods. Compounds of formula VIII are commercially available or may be prepared according to the following Scheme 8.

Scheme 8

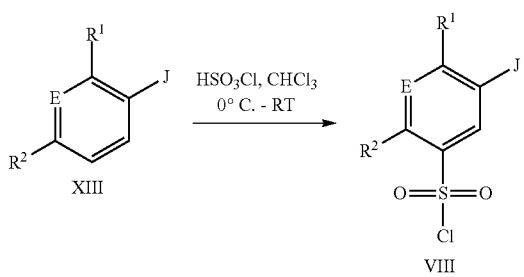

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the present invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere. At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound.

In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds of the present invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

The compounds of the present invention inhibit PI 3-kinase gamma isoform selectively as indicated in in vitro and in vivo tests as provided herein.

Thus, the compounds of the present invention may be useful in the treatment of conditions which are mediated by the activation of PI 3-kinase gamma isoform, particularly inflammatory or allergic conditions.

Compounds of the present invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, compounds of the present invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the present invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Compounds of the present invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with compounds of the present invention include thrombosis, hypertension, heart ischaemia and pancreatitis, (Nature review November 2006 Vol 5), treatment of anaemia including haemolytic anaemia, aplastic anaemia and pure red cell anaemia (WO 2006/040318), septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

Agents of the present invention may be useful in the treatment or prevention of heart failure such as (acute and chronic) congestive heart failure, left ventricular dysfunction including impaired cardiac contractility, hypertrophic cardiomyopathy, diabetic cardiac myopathy and other types of detrimental cardiac dysfunction and remodelling.

Other diseases or conditions which may be treated with compounds of the present invention include septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The compounds of the present invention may also be useful in the treatment of visceral disorders, inflammatory bowel disease, inflammatory bowel disorder, cystitis, e.g. interstitial cystitis and urinary incontinence including bladder detrusor hyper-reflexia and bladder hypersensitivity.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cemadas et al (1999) *Am. J. Respir. Cell Mol. Biol.* 20:1-8.

The compounds of the present invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosage or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition.

Useful combinations of PI 3-kinase inhibitors with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl]tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

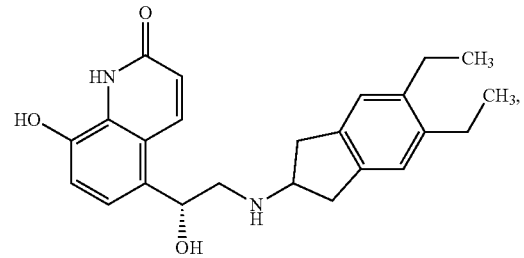 [SMILES: CCc1cc2c(cc1CC)CC(NC[C@H](O)c1ccc(O)c3[nH]c(=O)ccc13)C2]

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841 Pi3 kinase inhibitors, e.g. those compounds of the invention, may be combined with an angiotensin receptor blocker, e.g. valsartan (an angiotensin receptor blocker) and achieve greater therapeutic effect than the administration of valsartan alone. The combination regimen also surprisingly reduces the rate of progression of cardiac, renal and cerebral end-organ damage. The combination elicits enhanced antihypertensive effects (whether malignant, essential, reno-vascular, diabetic, isolated systolic, or other secondary type of hypertension) and lessening of pulse pressure. The combination is also effective in treating supraventricular and ventricular arrhythmias, atrial fibrillation, atrial flutter or detrimental vascular remodeling. It can further be shown that the combination is beneficial in the treatment and prevention of myocardial infarction and its sequelae, and is useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy provides benefit in diseases in which normal endothelial function is disrupted such as heart failure, angina pectoris and diabetes. Furthermore, the combination may be used for the treatment or prevention of primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke.

Compounds of the present invention may also be useful in the treatment of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, Graves ophthalmopathy, alopecia areata and others, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis and further eczematous dermatitises, seborrhoeic dermatitis, cutaneous manifestations of immunologically-mediated disorders, inflammatory eye disease, myocarditis or hepatitis, gut ischemia, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Compounds of the present invention may be administered in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, biolimus-7 or biolimus-9; an ascomycin having immuno-suppressive properties, e.g. ABT-281 or ASM981; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a S1P receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists.

The compounds of the present invention may also be useful in the treatment of visceral disorders, inflammatory bowel disease, inflammatory bowel disorder, cystitis, e.g. interstitial cystitis and urinary incontinence including bladder detrusor hyperreflexia and bladder hypersensitivity.

The compounds of the present invention may also be used in the treatment of anaemia, according to WO2006/040318.

The compounds of the present invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

Thus, in a further aspect, there is provided a compound of the present invention for use in therapy. In a further embodiment, the therapy is selected from a disease or disorder which is mediated by the activation of PI 3-kinase gamma isoform. In a further embodiment, the therapy is selected from a disease which may be treated by inhibiting of PI 3-kinase gamma isoform. In another embodiment, the therapy is selected from a disease which may be treated by inhibiting of PI 3-kinase gamma isoform selectively over PI 3-kinase delta isoform.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the activation of PI 3-kinase, particularly the gamma isoform, or (ii) associated with PI 3-kinase gamma isoform activity, or (iii) characterized by activity (normal or abnormal) of PI 3-kinase gamma isoform; or (2) reducing or inhibiting the activity of PI 3-kinase gamma isoform. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PI 3-kinase gamma isoform.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the present invention may be useful as pharmaceuticals and are thus usually formulated in the form of a pharmaceutical composition.

Hence, in another aspect, the present invention provides a pharmaceutical composition comprising a compound of the present invention and a pharmaceutically acceptable carrier.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in a mixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

Hence, the invention also includes (A) an agent of the invention, or a pharmaceutically acceptable salt or solvate thereof, in inhalable form; (B) an inhalable medicament comprising a compound of the present invention in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of compounds of the present invention employed in practicing the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In a further aspect, there is provided a pharmaceutical combination comprising a compound of the present invention and at least one other therapeutic agent, for example for simultaneous, separate or sequential use in therapy. In one embodiment, the therapy is the treatment of a disease or disorder mediated by the activation of PI 3-kinase, particularly the gamma isoform. Products provided as a pharmaceutical combination include a composition comprising the compound of the present invention and the other therapeutic agent(s) together in the same pharmaceutical composition, or the compound of the present invention and the other therapeutic agent(s) in separate form, e.g. in the form of a kit.

In one embodiment, the invention provides a pharmaceutical combination comprising a compound of the present invention and another therapeutic agent(s). Optionally, the pharmaceutical composition may comprise a pharmaceutically acceptable excipient, as described above.

In one embodiment, there is provided a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like.

The kit may be used for administering different dosage forms, for example, oral and parenteral, for administering the separate compositions at different dosage intervals, or for titrating the separate compositions against one another. To assist compliance, the kit of the invention typically comprises directions for administration.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound of the present invention, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

PI 3-kinase antagonists such as the compounds of the present invention are also useful as co-therapeutic agents for use in combination with a second active agent such as for example an organic nitrate and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO— and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein (a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In a particular embodiment, there is provided a pharmaceutical combination comprising the compounds of the present invention and a second agent wherein the second agent is a PDE 5 inhibitor or neutral endopeptidase inhibitor.

The compounds of the present invention may be mixed with a second agent in a fixed pharmaceutical composition or it may be administered separately, before, simultaneously with or after the other drug substance.

Particularly, the invention includes in a further aspect a combination of a PI 3-kinase inhibitor such a compound of the present invention with osmotic agents (hypertonic saline, dextran, mannitol, Xylitol), ENaC blockers, an anti-inflammatory, bronchodilatory, antihistamine, anti-tussive, antibiotic and/or DNase drug substance, wherein the TPH1 antagonist and the further drug substance may be in the same or different pharmaceutical composition.

Suitable antibiotics include macrolide antibiotics, e.g., tobramycin (TOBITm).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Accordingly, the invention includes as a further aspect a combination of PI 3-kinase inhibitors such the compounds of the present invention with second agents that are IP receptor agonist, particularly the compounds disclosed in WO2012/007539.

Accordingly, the invention includes as a further aspect a combination of PI 3-kinase inhibitors such the compounds of the present invention with second agents that are multi-kinase inhibitors, such as imatinib mysilate, Gleevec. Imatinib functions as a specific inhibitor of a number of tyrosine kinase enzymes. It occupies the TK active site, leading to a decrease in activity. TK enzymes in the body, include the insulin receptor. Imatinib is specific for the TK domain in the Abelson proto-oncogene, c-kit and PDGF-R (platelet-derived growth factor receptor).

In a particular embodiment, there is provided a pharmaceutical combination comprising a compound of the present invention and a second active agent selected from phosphodiesterase V inhibitors, neutral endopeptidase 1 inhibitors, ALK-5 inhibitors, rho-kinase inhibitors, TPH1 inhibitors, multi-kinase inhibitors, endothelin antagonist, diuretic, aldosteron receptor blocker, and endothelin receptor blocker.

In another embodiment, there is provided a pharmaceutical combination comprising a compound of the present invention and a second active agent selected from phosphodiesterase V inhibitors, neutral endopeptidase 1 inhibitors, ALK-5 inhibitors, rho-kinase inhibitors, TPH1 inhibitors, multi-kinase inhibitors.

Compounds according to any one of embodiments 1-13 where both $R^3$ and $R^4$ are H have been found to be metabolites of the compounds of the present invention.

EXPERIMENTAL

The compounds of the present invention are illustrated by the following example compounds.

From the foregoing it will be appreciated that, although specific embodiments of the invention have been described herein for purposes of illustration, various modifications may be made without deviating from the spirit and scope of the invention. Accordingly, the invention is not limited except as by the appended claims.

General Conditions:

Mass spectra were run on LCMS systems using electrospray ionization. These were either Agilent 1100 HPLC/Micromass Platform Mass Spectrometer combinations or Waters Acquity UPLC with SQD Mass Spectrometer. [M+H] refers to mono-isotopic molecular weights. NMR spectra were run on Bruker AVANCE 400 MHz or 500 MHz NMR spectrometers using ICON-NMR. Spectra were measured at 298K and were referenced using the solvent peak.

As a person skilled in the art understands, when running a $^1$H NMR in deuterated DMSO for compounds according to any one of embodiments 1-36 with $R^1$=methyl, the signal of said methyl protons is often obscured due to the DMSO solvent peak at δ of around 2.5 ppm.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 30 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations

AcOH acetic acid
aq. aqueous
br broad
BuOH butanol
conc. concentrated
d doublet
DCM dichloromethane
DCC N,N'-dicyclohexylcarbodiimide
DCE 1,2-dichloroethane
DEAD diethyl azodicarboxylate
DIPEA diisopropylethylamine
DMA dimethylacetamide
DME 1,2-dimethoxyethane
DMF N,N-dimethylformamide
DMSO dimethylsulfoxide
Et$_2$O diethyl ether
EtOAc ethyl acetate
EtOH ethanol
h hour(s)
HATU 0-(7-azabenzotriazol-1-yl)-N,N,N,N-tetramethyluronium hexafluorophosphate
HOBt.H$_2$O 1-Hydroxybenzotriazole hydrate
HPLC High Performance Liquid Chromatography
KOAc Potassium acetate
KOtBu Potassium tert-butoxide
LCMS liquid chromatography and mass spectrometry
MeOH methanol
MeCN acetonitrile
MS mass spectrometry
m multiplet
min minute
ml milliliter(s)
m/z mass to charge ratio
NBS N-bromosuccinimide
NMR nuclear magnetic resonance
PdCl$_2$(dppOCH$_2$Cl$_2$ adduct [1,1-Bis(diphenylphosphino)ferrocene]dichloropalladium (II) dichloromethane adduct.
Pd(PPh$_3$)$_2$Cl$_2$ Bis(triphenylphosphine)palladium(II) dichloride
ppm parts per million
PS polymer supported
Rt retention time
RT room temperature
s singlet
sat. saturated
SCX-2 strong cation exchange (e.g. Isolute® SCX-2 columns from Biotage)
t triplet
TBME methyl-tert-butyl ether
TEA triethylamine
TFA trifluoroacetic acid
THF tetrahydrofuran
TLC thin layer chromatography Referring to the examples that follow, compounds of the preferred embodiments were synthesized using the methods described herein, or other methods, which are known in the art. The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

Where microwave heating was employed, this was carried out using a Biotage Initiator Sixty microwave in dedicated reaction vials at the temperature shown and for the time indicated.

If not indicated otherwise, the analytical LCMS conditions are as follows:

Method A

| | |
|---|---|
| Column: | Cynergi 2.5 uMMax-RP100A(20 × 4.0)mm. |
| Mobile Phase: | A: Water + 0.1% Formic Acid B: Acetonitrile |
| Gradient | 0.0-0.5 min 20% B, 2.5-4.5 mins 95% B, 5.0 min 20% B |

Method 2minLC_v003

| | |
|---|---|
| Column | Waters BEH C18 50 × 2.1 mm, 1.7 μm |
| Column Temperature | 50° C. |
| Eluents | A: H$_2$O, B: acetonitrile, both containing 0.1% TFA |
| Flow Rate | 0.8 ml/min |
| Gradient | 0.20 min 5% B; 5% to 95% B in 1.30 min, 0.25 min 95% B |

Method 2minLowpH

| | |
|---|---|
| Column: | Waters Acquity CSH 1.7 μm, 2.1 × 50 mm |
| Temperature: | 50° C. |
| Mobile Phase: | A: Water + 0.1% Formic Acid B: Acetonitrile + 0.1% Formic Acid |
| Flow rate: | 1.0 mL/min |
| Gradient: | 0.0 min 5% B, 0.2-1.3 min 5-98% B, 1.3-1.55 min 98% B, 1.55-1.6 min 98-5% B |

Method 2minLowpFlv01

| | |
|---|---|
| Column: | Waters Acquity CSH 1.7 μm, 2.1 × 50 mm |
| Temperature: | 50° C. |
| Mobile Phase: | A: Water + 0.1% Formic Acid B: Acetonitrile + 0.1% Formic Acid |
| Flow rate: | 1.0 mL/min |
| Gradient: | 0.0 min 5% B, 0.2-1.55 min 5-98% B, 1.55-1.75 min 98% B, 1.75-1.8 min 98-5% B |

Method 2minLowpFlv02

| | |
|---|---|
| Column: | Acquity CSH C18 50 × 2.1 mm |
| Temperature: | 50° C. |
| Eluents | A: Water B: Acetonitrile both with + 0.1% TFA |
| Flow Rate: | 1.0 mL/min |
| Gradient: | 0.0 min 5% B, 0.2-1.55 min 5-98% B, 1.55-1.75 min 98% B, 1.75-1.8 min 98-5% B |

Method 10minLowpH

| | |
|---|---|
| Column: | Waters Acquity CSH 1.7 μm, 2.1 × 100 mm |
| Temperature: | 50° C. |
| Mobile Phase: | A: Water + 0.1% Formic Acid B: Acetonitrile + 0.1% Formic Acid |
| Flow rate: | 0.7 mL/min |
| Gradient: | 0.0 min 2% B, 0.5-8.0 min 2-98% B, 8.0-9.0 min 98% B, 9.0-9.1 min 98-2% B |

Method 10minHighpH

| | |
|---|---|
| Column: | Waters Acquity CSH 1.7 μm, 2.1 × 100 mm |
| Temperature: | 50° C. |
| Mobile Phase: | A: Water + 0.1% Ammonia B: Acetonitrile + 0.1% Ammonia |
| Flow rate: | 0.7 mL/min |
| Gradient: | 0.0 min 2% B, 0.5-8.0 min 2-98% B, 8.0-9.0 min 98% B, 9.0-9.1 min 98-2% B |

If not indicated otherwise, the analytical reverse phase preparative HPLC conditions are as follows:

Method 10-35% Gradient lowpH

| | |
|---|---|
| Column: | Waters Sunfire C18, 150 × 30 mm, 5 mic |
| Mobile Phase: | A = 0.1% TFA in Water, B = 0.1% TFA in MeCN |
| Gradient: | 0.0-0.5 min 10% B 30 mL/min, 0.5-1.0 min 10% B 30-50 mL/min, 1.0-7.25 min 10-35% B, 7.25-7.3 min 35-98% B, 7.3-8.3 min 98% B, 8.3-8.5 min 98-100% B 50 mL/min |

Example 1

N-(3-Hydroxy-propyl)-4-methyl-3-[6-(2-methyl-thiazol-5-yl)-pyrazin-2-yl]-benzenesulfonamide To a 2-5 ml microwave vial was added 2-methyl-5-(4,4,5,5-tetramethyl-1,3,2-dioxaborolan-2-yl)thiazole (116 mg, 0.517 mmol), 2-bromo-6-chloropyrazine (100 mg, 0.517 mmol), Na2CO3 (0.775 ml, 1.551 mmol, 2M) and PdCl$_2$ (dppf). CH$_2$Cl$_2$ adduct (21 mg, 0.026 mmol) in DME (3 ml) to give an orange suspension. The reaction was heated in a biotage initiator microwave at 120° C. for 60 mins. To the reaction was added N-(3-hydroxypropyl)-4-methyl-3-(4,4,5,5-tetramethyl-1,3,2-dioxaborolan-2-yl)benzenesulfonamide (Intermediate B1) (184 mg, 0.517 mmol) and PdCl$_2$(dppf) CH$_2$Cl$_2$ adduct (21 mg, 0.026 mmol). The reaction was heated at 120° C. in a microwave for 60 mins. The reaction was extracted into ethyl acetate, washed with water, brine, dried over MgSO$_4$, filtered and the solvent removed under reduced pressure. The crude product was loaded onto silica and purified by flash column chromatography using a Teledyne ISCO combiflash Rf, elution with TBME:MeOH (0-20%) over 15 mins on a 12 g silica cartridge. The required fractions were combined and the solvent removed under reduced pressure to yield a brown oil which was dried under reduced pressure at 40° C. for 2 hours. The product was isolated as a brown solid.

LCMS: Rt 0.86 mins; MS m/z 405.2 [M+H]+; Method LowpH_v002.

$^1$H NMR (400 MHz, DMSO) δ (ppm) 9.30 (1H, s), 8.78 (1H, s), 8.57 (1H, s), 7.91 (1H, s), 7.82-7.79 (1H, dd), 7.63-7.61 (1H, d), 7.57-7.54 (1H, m), 4.42-4.40 (1H, m), 3.40-3.35 (2H, m), 2.85-2.80 (2H, m), 2.72 (3H, s), 2.49 (3H, s), 1.57-1.51 (2H, m).

Example 2

3-[6-(1,3-Dimethyl-1H-pyrazol-4-yl)-pyrazin-2-yl]-N-(2-hydroxy-2-methyl-propyl)-4-methyl-benzenesulfonamide

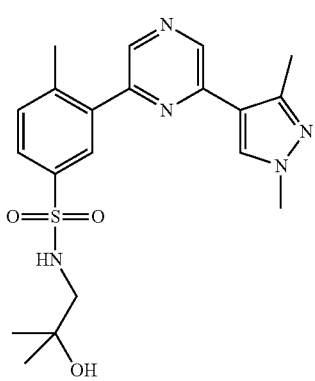 [SMILES: Cc1ccc(S(=O)(=O)NCC(C)(C)O)cc1-c1cncc(-c2cn(C)nc2C)n1]

To a 0.5-2 ml microwave vial was added N-(2-hydroxy-2-methylpropyl)-4-methyl-3-(4,4,5,5-tetramethyl-1,3,2-dioxaborolan-2-yl)benzenesulfonamide (Intermediate B2) (150 mg, 0.406 mmol), 2-chloro-6-(1,3-dimethyl-1H-pyrazol-4-yl)pyrazine (Intermediate C1) (85 mg, 0.406 mmol) PdCl$_2$(dppf).CH$_2$Cl$_2$ adduct (16.59 mg, 0.020 mmol), 2M aq. Na$_2$CO$_3$ (0.609 ml, 1.219 mmol) in DME (1.3 ml). The reaction was heated at 120° C. for 45 mins in a biotage initiator microwave (fixed hold time on, 30 s pre stir, high absorption). The reaction was combined with water (10 ml) and extracted into EtOAc (10 ml). The organic extracts were then washed with brine (15 ml) before being dried over magnesium sulfate and concentrated in vacuo. The reaction was purified by flash column chromatography using a Teledyne ISCO combiflash Rf, elution with Hexane/EtOAc (0-100%) over 15 mins on a 12 g silica cartridge. The required fractions were combined and concentrated in vacuo before being dried in a vacuum oven at 40° C. for 3 hours to give the product.

LCMS: Rt 0.94 mins; MS m/z 416.4 [M+H]+; Method 2minLowpHv01

$^1$H NMR (400 MHz, d6-DMSO) d (ppm) 8.90 (1H, s), 8.63 (1H, s), 8.41 (1H, s), 7.94 (1H, d), 7.79 (1H, dd), 7.59 (1H, d), 7.51 (1H, br), 4.42 (1H, br), 3.84 (3H, s), 2.63 (2H, br), 2.49 (3H, s), 2.46 (3H, s), 1.05 (6H, s).

Example 3

3-[6-(1,3-Dimethyl-1H-pyrazol-4-yl)-pyrazin-2-yl]-N-(3-hydroxy-3-methyl-butyl)-4-methyl-benzenesulfonamide

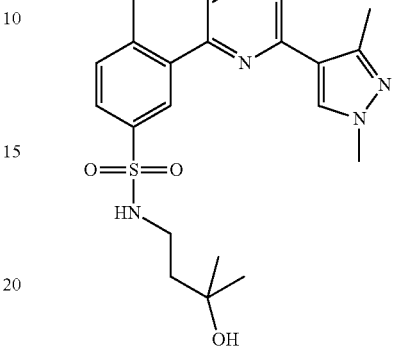

The title compound was prepared from N-(3-Hydroxy-3-methylbutyl)-4-methyl-3-(4,4,5,5-tetramethyl-1,3,2-dioxaborolan-2-yl)benzenesulfonamide (Intermediate B3) and 2-Chloro-6-(1,3-dimethyl-1H-pyrazol-4-yl)-pyrazine (Intermediate C1) under analogous conditions to those of Example 2.

LCMS: Rt 0.96 mins; MS m/z 430.4 [M+H]+; Method 2minLowpHv01

$^1$H NMR (400 MHz, d6-DMSO) δ 8.91 (1H, s), 8.63 (1H, s), 8.41 (1H, s), 7.92 (1H, d), 7.80 (1H, dd), 7.62 (1H, d), 7.47 (1H, t), 4.28 (1H, s), 3.84 (3H, s), 2.85 (2H, m), 2.47 (3H, s), 1.51 (2H, m), 1.02 (6H, s) one methyl group is obscured under the DMSO solvent peak.

Example 4

Trans 3-[6-(1,3-Dimethyl-1H-pyrazol-4-yl)-pyrazin-2-yl]-4-methyl-N-(3-methyl-oxetan-3-ylmethyl)-benzenesulfonamide

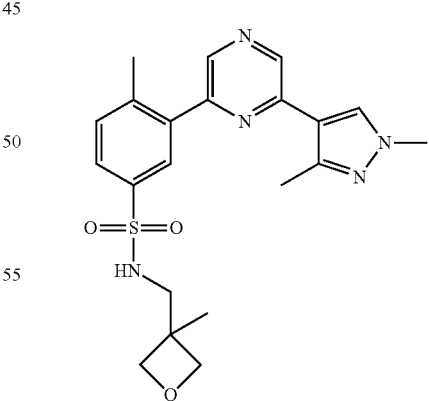

The title compound was prepared from 4-Methyl-N-(3-methyl-oxetan-3-ylmethyl)-3-(4,4,5,5-tetramethyl-[1,3,2]dioxaborolan-2-yl)-benzenesulfonamide (Intermediate B4) and 2-Chloro-6-(1,3-dimethyl-1H-pyrazol-4-yl)-pyrazine (Intermediate C1) under analogous conditions to those of Example 2.

LCMS: Rt 0.96 mins; MS m/z 428.2 [M+H]+; Method 2minLowpHv01

$^1$H NMR (400 MHz, CDCl$_3$), δ 8.79 (1H, s), 8.55 (1H, s), 8.04 (1H, s), 7.95 (1H, s), 7.88 (1H, dd), 7.53 (1H, d), 4.73 (1H, br t), 4.39 (4H, m), 3.95 (3H, s), 3.21 (2H, d), 2.61 (3H, s), 2.55 (3H, s), 1.29 (3H, s).

Example 5

Trans N-(4-Hydroxycyclohexyl)-4-methyl-3-(6-(2-methylthiazol-5-yl)pyrazin-2-yl)benzenesulfonamide

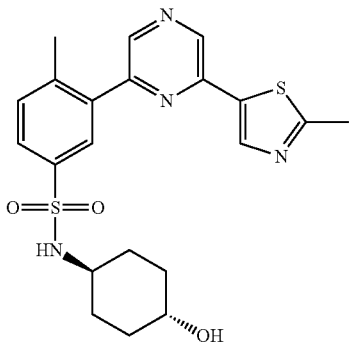 [SMILES: Cc1ncc(-c2cncc(-c3cc(S(=O)(=O)N[C@H]4CC[C@H](O)CC4)ccc3C)n2)s1]

To a solution of trans 3-(6-chloropyrazin-2-yl)-N-(4-hydroxycyclohexyl)-4-methylbenzenesulfonamide (Intermediate D2) (150 mg, 0.393 mmol) was added 2-methyl-5-(4,4,5,5-tetramethyl-1,3,2-dioxaborolan-2-yl)thiazole (97 mg, 0.432 mmol), bis(triphenylphosphine)palladium(II) chloride (13.79 mg, 0.020 mmol) and Na$_2$CO$_3$ (aq. 2.0M) (589 μL, 1.178 mmol). The reaction was heated in a microwave at 150° C. for 30 minutes. The reaction was added to sat. aqueous Na$_2$CO$_3$ (50 ml), and the product extracted into EtOAc (2×50 ml). The organic phases were washed with brine, dried over MgSO$_4$, and concentrated under vacuo. The crude product was purified by ISCO combiflash chromatography, eluting with a modified 0-10% gradient (DCM-2M NH$_3$ in MeOH) on a 12 g silica column, loading with DCM. The resulting clear oil was sonicated in TBME (5 ml), and scratched with a spatular until a fine white precipitate was formed and then the mixture was left to stand. The resulting solid collected by filtration, washed with a small amount of TBME and dried.

LCMS: Rt 0.89 mins; MS m/z 445.3 [M+H]+; Method 2minLowpH $^1$H NMR (400 MHz, DMSO-d6) δ9.29 (1H, s), 8.77 (1H, s), 7.56 (1H, s), 7.95 (1H, s), 7.83 (1H, d), 7.66 (1H, br s), 7.60 (1H, d), 4.55 (1H, d), 3.36-3.26 (1H, m), 3.01-2.90 (1H, m), 2.72 (3H, s), 2.49 (3H, s), 1.77-1.60 (4H, m), 1.27-1.03 (4H, m).

Example 6

3-[6-(1,3-Dimethyl-1H-pyrazol-4-yl)-pyrazin-2-yl]-N-(6-hydroxy-spiro[3.3]hept-2-yl)-4-methyl-benzenesulfonamide

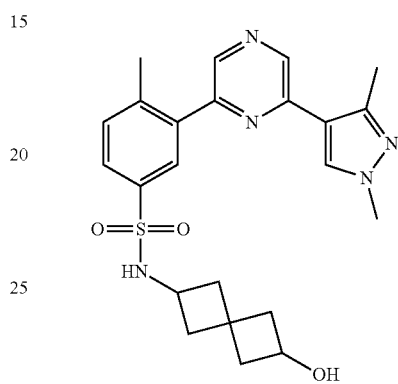

A stirring mixture of 3-bromo-N-(6-hydroxyspiro[3.3]heptan-2-yl)-4-methylbenzenesulfonamide (Intermediate A6) (200 mg, 0.555 mmol), KOAc (82 mg, 0.833 mmol), PdCl$_2$(dppf).CH$_2$Cl$_2$ adduct (22.67 mg, 0.028 mmol), and bis(pinocalato)diboron (155 mg, 0.611 mmol) in DME (2776 μL), under N$_2$, was heated at 90° C. for 18 h. 2-Chloro-6-(1,3-dimethyl-1H-pyrazol-4-yl)pyrazine (Intermediate C1) (116 mg, 0.555 mmol), 2M aqueous Na$_2$CO$_3$ (833 μL, 1.665 mmol), and PdCl$_2$(dppf).CH$_2$Cl$_2$ adduct (22.67 mg, 0.028 mmol) was added and reaction was heated in a microwave for 45 mins at 120° C. The reaction was added to water (80 ml), and product extracted into EtOAc (2×70 ml). The organic phase was washed with brine, dried over MgSO$_4$ and polymer supported trimethyl thiol to scavenge Pd. This mixture was swirled occasionally over 1 hour. The solids were removed by filtration, washed with EtOAc and concentrated under vacuo. The crude product was purified by ISCO combiflash chromatography, eluting with 0-10% gradient of (2M NH$_3$ in MeOH) in DCM on a 12 g silica column, loading with DCM. To give the product as a solid.

LCMS: Rt 0.93 mins; MS m/z 455.5 [M+H]+; Method 2minLowpHv01

$^1$H NMR (400 MHz, d6-DMSO) δ 8.91 (1H, s), 8.62 (1H, s), 8.42 (1H, s), 7.88 (2H, m), 7.77 (1H, d), 7.58 (1H, d), 4.83 (1H, d), 3.84 (4H, m), 3.52 (1H, m), 2.47 (3H, s), 2.21 (1H, m), 2.02 (2H, m), 1.90 (1H, m), 1.71 (4H, m) one methyl group obscured under the DMSO solvent peak.

Example 7

Cis 3-[6-(1,3-Dimethyl-1H-pyrazol-4-yl)-pyrazin-2-yl]-N-(3-hydroxy-cyclobutylmethyl)-4-methyl-benzenesulfonamide

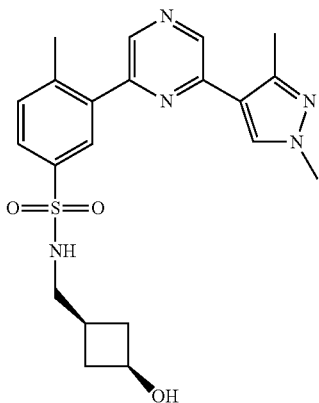 [SMILES: Cc1ccc(S(=O)(=O)NC[C@H]2C[C@@H](O)C2)cc1-c1cncc(-c2cn(C)nc2C)n1]

The title compound was prepared from Cis 3-Bromo-N-(3-hydroxy-cyclobutylmethyl)-4-methyl-benzenesulfonamide (intermediate A7) and 2-Chloro-6-(1,3-dimethyl-1H-pyrazol-4-yl)-pyrazine (Intermediate C1) under analogous conditions to those of Example 6.

LCMS: Rt 1.01 mins m/z 430.3 [M+H]+; Method 2min-LowpHv01

$^1$H NMR (400 MHz, d6-DMSO) δ 8.91 (1H, s), 8.63 (1H, s), 8.42 (1H, s), 7.91 (1H, d), 7.78 (1H, dd), 7.59 (2H, m), 4.90 (1H, d), 3.84 (3H, s), (3.84 (1H, m (presumed to be under 3H peak)), 2.76 (2H, t), 2.47 (3H, s), 2.17 (2H, m), 1.75 (1H, m), 1.41 (2H, m), one methyl group is obscured under the DMSO solvent peak.

Example 8

3-[6-(1,3-Dimethyl-1H-pyrazol-4-yl)-pyrazin-2-yl]-N-(3-hydroxy-2,2-dimethyl-propyl)-4-methyl-benzenesulfonamide

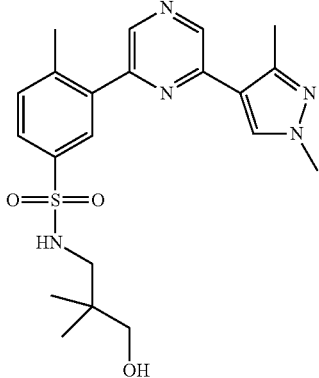 [SMILES: Cc1ccc(S(=O)(=O)NCC(C)(C)CO)cc1-c1cncc(-c2cn(C)nc2C)n1]

The title compound was prepared from 3-Bromo-N-(3-hydroxy-2,2-dimethyl-propyl)-4-methyl-benzenesulfonamide (intermediate A8) and 2-Chloro-6-(1,3-dimethyl-1H-pyrazol-4-yl)-pyrazine (Intermediate C1) under analogous conditions to those of Example 6.

LCMS: Rt 0.99 mins m/z 430.4 [M+H]+; Method 2min-LowpHv01

$^1$H NMR (400 MHz, d6-DMSO), δ 8.91 (1H, s), 8.63 (1H, s), 8.42 (1H, s), 7.93 (1H, d), 7.80 (1H, dd), 7.60 (1H, d), 7.41 (1H, t), 4.45 (1H, t), 3.84 (3H, s), 3.10 (2H, d), 2.59 (2H, d), 2.47 (3H, s), 0.77 (6H, s)

Example 9

N-(3-Hydroxy-3-methyl-butyl)-4-methyl-3-{6-[1-(2-morpholin-4-yl-ethyl)-1H-pyrazol-4-yl]-pyrazin-2-yl}-benzenesulfonamide

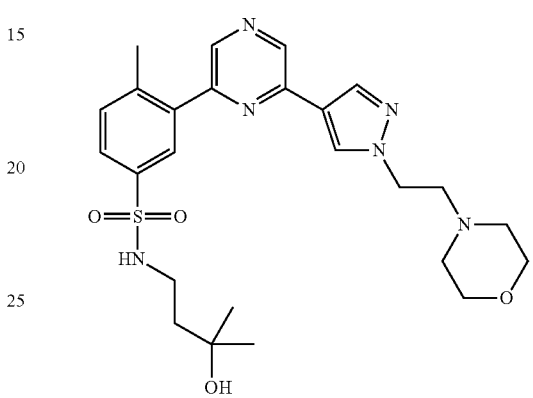

The title compound was prepared from 3-(6-Chloro-pyrazin-2-yl)-N-(3-hydroxy-3-methyl-butyl)-4-methyl-benzenesulfonamide (Intermediate D1) and 4-{2-[4-(4,4,5,5-Tetramethyl-[1,3,2]dioxaborolan-2-yl)-pyrazol-1-yl]-ethyl}morpholine under analogous conditions to those of Example 5.

LCMS: Rt 0.63 mins; MS m/z 515.4 [M+H]+; Method 2minLC_v003.

$^1$H NMR (400 MHz, CDCl$_3$) δ8.79 (1H, s), 8.55 (1H, s), 8.18 (1H, br s), 8.10 (1H, s), 8.05 (1H, d), 7.38 (1H, dd), 7.50 (1H, d), 5.62 (1H, br t), 4.35 (2H, br s), 3.71 (4H, br s), 3.19 (2H, m), 2.89 (2H, br s), 2.55 (3H, s), 2.53 (4H, br s), 1.65 (2H, m), 1.19 (6H, s), OH is exchanged.

Example 10

N-(3-Hydroxy-3-methyl-butyl)-4-methyl-3-{6-[3-methyl-1-(2-morpholin-4-yl-ethyl)-1H-pyrazol-4-yl]-pyrazin-2-yl}-benzenesulfonamide

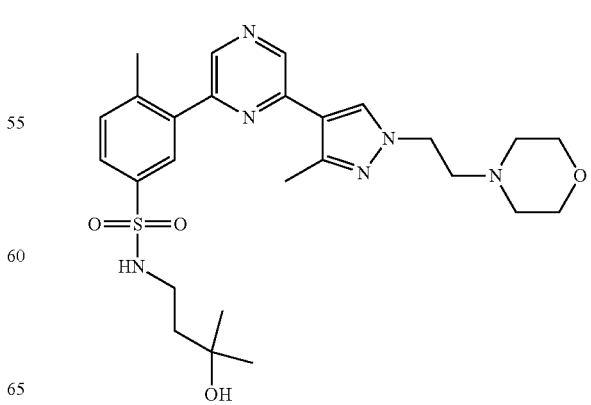

To a solution of 4-(2-(4-(6-bromopyrazin-2-yl)-5-methyl-1H-pyrazol-1-yl)ethyl)morpholine (Intermediate C2) (50 mg, 0.142 mmol) in Toluene/EtOH (2:1; 1.5 ml) was added N-(3-hydroxy-3-methylbutyl)-4-methyl-3-(4,4,5,5-tetramethyl-1,3,2-dioxaborolan-2-yl)benzenesulfonamide (Intermediate B3) (54.4 mg, 0.142 mmol) followed by Pd(PPh$_3$)$_2$Cl$_2$ (5 mg, 7.10 μmol) and 2M aqueous sodium carbonate solution (0.213 ml, 0.426 mmol). The reaction was heated in the microwave at 100° C. for 30 minutes. The reaction was diluted with ethyl acetate, washed with water and the organic layer concentrated under reduced pressure. The residue was purified by flash chromatography on silica gel (12 g) using ISCO combiflash eluting with DCM/MeOH gradient (0-10%) to give the product.

LCMS: Rt 0.70 mins; MS m/z 529.3 [M+H]+; Method 2minLowpHv01

$^1$H NMR (400 MHz, DMSO-d6): δ 8.91 (1H, s), 8.62 (1H, s), 8.47 (1H, s), 7.93 (1H, d), 7.79 (1H, dd), 7.62 (1H, d), 7.46 (1H, br s), 4.28 (1H, br s), 4.21 (2H, t), 3.56 (4H, t), 2.85 (2H, br t), 2.73 (2H, t), 2.50 (3H, s partially obscured by DMSO), 2.48 (3H, s), 2.42 (4H, t), 1.50 (2H, t), 1.01 (6H, s).

Example 11

Trans N-(4-Hydroxy-cyclohexyl)-4-methyl-3-(6-pyridin-3-yl-pyrazin-2-yl)-benzenesulfonamide

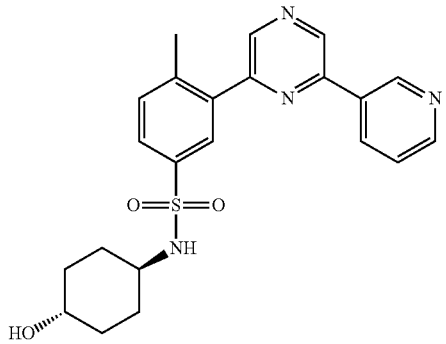 [SMILES: Cc1ccc(S(=O)(=O)N[C@H]2CC[C@H](O)CC2)cc1-c1cncc(-c2cccnc2)n1]

A red suspension of Trans N-(4-hydroxycyclohexyl)-4-methyl-3-(4,4,5,5-tetramethyl-1,3,2-dioxaborolan-2-yl)benzenesulfonamide (Intermediate B5) (204 mg, 0.517 mmol), 3-(4,4,5,5-tetramethyl-1,3,2-dioxaborolan-2-yl)pyridine (106 mg, 0.517 mmol), 2M aq. NaHCO$_3$ (1.3 ml, 2.58 mmol) and PdCl$_2$(dppf).CH$_2$Cl$_2$ adduct (21.11 mg, 0.026 mmol) in 1,2-dimethoxyethane (2.53 mL), under N$_2$, was heated in a microwave at 120° C. for 0.75 h. 3-(4,4,5,5-Tetramethyl-1,3,2-dioxaborolan-2-yl)pyridine (106 mg, 0.517 mmol) and PdCl$_2$(dppf).CH$_2$Cl$_2$ adduct (21.11 mg, 0.026 mmol) were added to the black suspension before heating to 120° C. for 0.75 hrs. Water (50 mL) was added followed by extracting twice with EtOAc (50 mL×2), washing with brine (20 mL) and drying over MgSO$_4$. The resulting organic phase was concentrated under reduced pressure. The crude product was purified by ISCO combiflash chromatography, eluting with a modified 0-10% gradient (DCM-N H$_3$ in MeOH) on a 12 g silica column, loading with DCM, to give the title compound.

LCMS: Rt 0.76 mins; MS m/z 425.5 [M+H]+; Method 2minLC_v003

$^1$H (400 MHz, d6-DMSO) δ 9.40 (2H, m), 8.95 (1H, s), 8.74 (1H, dd), 8.57 (1H, m). 8.03 (1H, d), 7.85 (1H, dd), 7.67 (1H, d), 7.62 (2H, m), 4.48 (1H, d), 3.30 (1H, m), 2.96 (1H, m), 2.55 (3H, s), 1.69 (4H, m), 1.14 (4H, m).

Example 12

Trans N-(4-Hydroxy-cyclohexyl)-4-methyl-3-[6-(5-morpholin-4-ylmethyl-thiophen-3-yl)-pyrazin-2-yl]-benzenesulfonamide

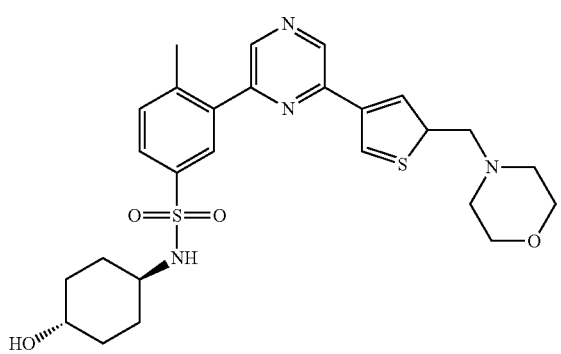

To a solution of Trans 3-(6-chloropyrazin-2-yl)-N-(4-hydroxycyclohexyl)-4-methylbenzenesulfonamide (Intermediate D2) (80 mg, 0.209 mmol) in DME (1047 μL) was added 4-((4-(4,4,5,5-tetramethyl-1,3,2-dioxaborolan-2-yl)thiophen-2-yl)methyl)morpholine (97 mg, 0.314 mmol), bis(triphenylphosphine)palladium(II) chloride (7.35 mg, 10.47 μmol) and Na$_2$CO$_3$ (aq. 2.0M) (66.6 mg, 0.628 mmol). The reaction was heated in a microwave at 120° C. for 30 mins. The reaction was added to water (50 ml), and product extracted into EtOAc (60 ml). The organic phase was washed with brine, dried over MgSO$_4$ and polymer supported trimethyl thiol to scavenge Pd. This mixture was swirled occasionally over 1 hour. The solids were removed by filtration, washed with EtOAc and concentrated under reduced pressure.

The crude product was purified by ISCO combiflash chromatography, eluting with a modified 0-10% gradient (DCM-2M NH$_3$ in MeOH) on a 12 g silica column, loading with DCM, to give a white solid.

LCMS: Rt 0.64 mins; MS m/z 529.3 [M+H]+; Method 2minLowpH $^1$H NMR (400 MHz, DMSO-d6) δ9.91 (1H, s), 8.75 (1H, s), 8.32 (1H, s), 7.98 (1H, s), 7.84 (1H, d), 7.69 (1H, s), 7.60 (1H, d), 4.52 (1H, s), 3.72 (2H, br s), 2.59 (4H, br s), 3.41 (1H, br s), 2.98 (1H, br s), 2.42 (4H, br s), 1.84-1.55 (4H, m), 1.30-1.10 (4H, m).

Example 13

Cis 3-[6-(2,5-Dimethyl-2H-pyrazol-3-yl)-pyrazin-2-yl]-N-(3-hydroxy-cyclobutylmethyl)-4-methyl-benzenesulfonamide

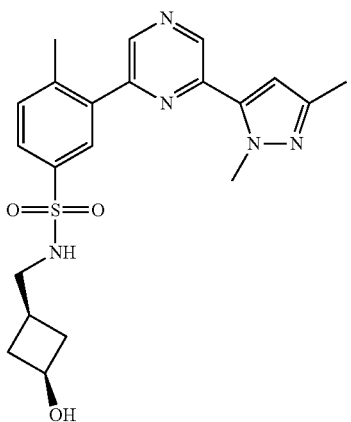 [SMILES: Cc1cc(-c2cncc(-c3cc(S(=O)(=O)NC[C@H]4C[C@@H](O)C4)ccc3C)n2)n(C)n1]

To a 0.5-2 ml microwave vial was added Cis 3-bromo-N-(3-hydroxycyclobutylmethyl)-4-methylbenzenesulfonamide (Intermediate A7) 150 mg, 0.449 mmol), 4,4,4',4',5,5,5',5'-octamethyl-2,2'-bi(1,3,2-dioxaborolane) (125 mg, 0.494 mmol), potassium acetate (66.1 mg, 0.673 mmol) and PdCl$_2$(dppf).CH$_2$Cl$_2$ adduct (18.33 mg, 0.022 mmol) in DME (1.3 ml) and the reaction heated at 120° C. for 1 hour in the biotage initiator microwave (fixed hold time on, 30 s pre-stir). To the reaction mixture was then added 2-chloro-6-(1,3-dimethyl-1H-pyrazol-5-yl)pyrazine (Intermediate C3) (94 mg, 0.449 mmol), PdCl$_2$(dppf).CH$_2$Cl$_2$ adduct (18.33 mg, 0.022 mmol) and 2M aqueous Na$_2$CO$_3$ (0.673 ml, 1.346 mmol). The reaction was heated at 120° C. for 1 hour in the biotage initiator microwave (fixed hold time on, 30 s pre-stir). The reaction was added to water (10 ml) and extracted into EtOAc (10 ml). The organic extracts were washed with brine (10 ml) before being dried over MgSO$_4$ and concentrated in vacuo.

The reaction was purified by flash column chromatography using the ISCO combiflash Rf, elution with Hexane/EtOAc (0-100%) over 15 mins on a 12 g silica cartridge to give the title compound.

LCMS: Rt 0.95 mins; MS m/z 429.3 [M+H]+; Method 2minLowpHv01

$^1$H NMR (400 MHz, d6-DMSO), δ 9.10 (1H, s), 8.84 (1H, s), 7.94 (1H, d), 7.81 (1H, dd), 7.61 (2H, m), 6.86 (1H, s), 4.90 (1H, d), 4.09 (3H, s), 3.84 (1H, m), 2.76 (2H, t), 2.23 (3H, s), 2.17 (2H, m), 1.74 (1H, m), 1.40 (2H, m), one methyl group is obscured under the DMSO solvent peak.

Preparation of Intermediates

Bromides A

Intermediate A1

3-Bromo-N-(3-hydroxypropyl)-4-methylbenzenesulfonamide

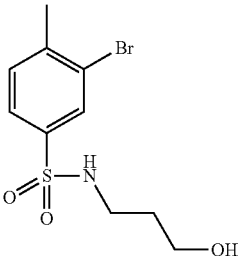 [SMILES: Cc1ccc(S(=O)(=O)NCCCO)cc1Br]

To a stirring solution of 3-bromo-4-methylbenzene-1-sulfonyl chloride (2 g, 7.42 mmol) in THF (37 mL) under N$_2$ was added 3-amino-1-propanol (0.568 ml, 7.42 mmol), DIPEA (1.56 ml, 8.9 mmol) and the resulting mixture was stirred at RT for 24 hours. The solvent was removed under reduced pressure and the crude material was added to 0.1M HCl (100 ml). The mixture was extracted with EtOAc (150 ml) and the organic extract was washed with sat. Na$_2$CO$_3$ (60 ml), brine, dried over MgSO$_4$ and concentrated under reduced pressure to afford the title compound;

LCMS: Rt 0.89 mins; MS m/z 310.1 [M+H]+; Method 2minLC_v003

Intermediate A2

3-Bromo-N-(2-hydroxy-2-methylpropyl)-4-methylbenzenesulfonamide

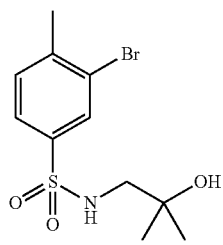 [SMILES: Cc1ccc(S(=O)(=O)NCC(C)(C)O)cc1Br]

To a stirring solution of 3-bromo-4-methylbenzene-1-sulfonyl chloride (3.02 g, 11.22 mmol) in pyridine (56 ml) under N$_2$ was added 1-amino-2-methylpropan-2-ol (1.0 g, 11.22 mmol) and the mixture was stirred at RT for 72 hours. The solvent was removed under reduced pressure and the resulting crude material was added to 0.1M HCl (100 ml). The mixture was extracted with EtOAc (150 ml) and the organic extract was washed with sat. Na$_2$CO$_3$ (100 ml), brine, dried over MgSO$_4$ and concentrated under reduced pressure to afford the title compound;

LCMS: Rt 1.01 mins; MS m/z 324.1 [M+H]+; Method 2minLC_v003

Intermediate A3

3-Bromo-N-(3-hydroxy-3-methyl-butyl)-4-methyl-benzenesulfonamide

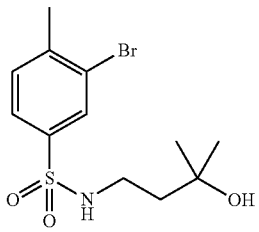 [SMILES: Cc1ccc(S(=O)(=O)NCCC(C)(C)O)cc1Br]

Prepared from 3-bromo-4-methylbenzene-1-sulfonyl chloride and 4-amino-2-methylbutan-2-ol analogously to Intermediate A2.

LCMS: Rt 1.04 mins; MS m/z does not ionise [M+H]+; Method 2minLC_v003

$^1$H NMR (400 MHz, DMSO-d6) δ 7.93 (1H, s), 7.70 (1H, d), 7.58 (1H, d), 7.52 (1H, br), 4.28 (1H, br), 2.80 (2H, m), 2.43 (3H, s), 1.49 (2H, m), 1.15 (6H, s).

Intermediate A4

3-Bromo-4-methyl-N-(3-methyl-oxetan-3-ylmethyl)-benzenesulfonamide

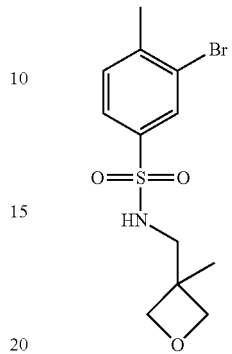

To a solution of (3-methyloxetan-3-yl)methanamine (2.026 g, 20.03 mmol) in DMA (50 ml) was added ethyl diisopropylamine (4.37 ml, 25.04 mmol). The mixture was stirred at RT for 30 min before adding 3-bromo-4-methyl-benzene-1-sulfonyl chloride (4.5 g, 16.70 mmol). The mixture was stirred at RT for 1 hr. The solvent was removed in vacuo and the residue was dissolved in EtOAc and washed with saturated aq. NaHCO$_3$ followed by 0.1M HCl then brine. The organic extract was dried over MgSO4 and the solvent removed to give the product as a pale yellow powder (5.19 g, 93%)

LCMS: Rt 1.10 mins; MS m/z 336.1 [M+H]+; Method 2minLowpHv01

The compounds of the following tabulated intermediates were prepared analogously to Intermediate A1 from the appropriate starting compounds:

TABLE 1

| Int. | Structure | Name | [M + H]+/NMR |
|---|---|---|---|
| A5 | 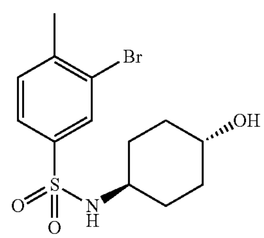 [SMILES: Cc1ccc(S(=O)(=O)N[C@H]2CC[C@H](O)CC2)cc1Br] | Trans 3-Bromo-N-(4-hydroxy-cyclohexyl)-4-methylbenzenesulfonamide | LCMS : Rt 1.01 mins; MS m/z 348.1 [M + H]+; Method 2minLC_v003 |
| A6 | 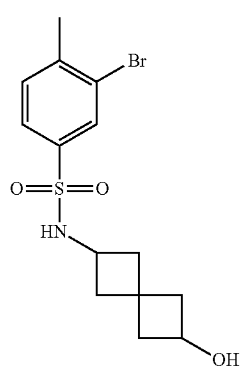 [SMILES: Cc1ccc(S(=O)(=O)NC2CC3(CC(O)C3)C2)cc1Br] | 3-Bromo-N-(6-hydroxy-spiro[3.3]hept-2-yl)-4-methyl-benzene-sulfonamide | LCMS: Rt 1.01 mins; MS m/z 360.3 [M + H]+; Method 2minLowpHv01 |

TABLE 1-continued

| Int. | Structure | Name | [M + H]⁺/NMR |
|---|---|---|---|
| A7 | 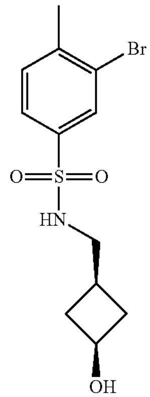 [SMILES: Cc1ccc(S(=O)(=O)NC[C@H]2C[C@@H](O)C2)cc1Br] | Cis 3-Bromo-N-(3-hydroxy-cyclobutylmethyl)-4-methyl-benzenesulfonamide | LCMS: Rt 0.91 mins; MS m/z 336.1 [M + H]+; Method 2minLC_v003 |
| A8 | 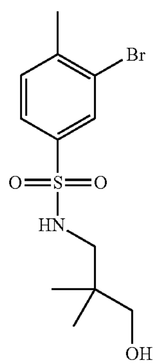 [SMILES: Cc1ccc(S(=O)(=O)NCC(C)(C)CO)cc1Br] | 3-Bromo-N-(3-hydroxy-2,2-dimethylpropyl)-4-methylbenzenesulfonamide | LCMS: Rt 0.98 mins; MS m/z 336.1 [M + H]+; Method 2minLC_v003 |

Boronic Esters (B)

Intermediate B1

N-(3-Hydroxypropyl)-4-methyl-3-(4,4,5,5-tetramethyl-1,3,2-dioxaborolan-2-yl)benzenesulfonamide

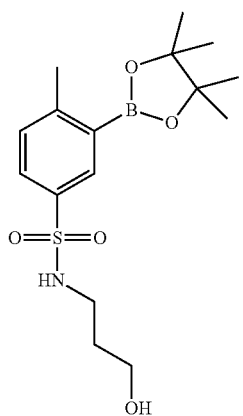 [SMILES: Cc1ccc(S(=O)(=O)NCCCO)cc1B1OC(C)(C)C(C)(C)O1]

A mixture comprising 3-bromo-N-(3-hydroxypropyl)-4-methylbenzenesulfonamide (Intermediate A1) (2.25 g, 7.30 mmol), KOAc (1.075 g, 10.95 mmol), PdCl₂(dppf).CH₂Cl₂ adduct (0.298 g, 0.365 mmol) and bis(pinacolato)diboron (2.039 g, 8.03 mmol) in DME (36.5 mL) under N2 was stirred at 90° C. for 5 hours. The resulting mixture was added to water (100 ml) and extracted with EtOAc (2×100 ml). The combined organic extracts were washed with brine, dried over MgSO₄ and concentrated under reduced pressure. Purification by chromatography on silica eluting with 0-100% gradient EtOAc in iso-hexane afforded the title compound;

LCMS: Rt 1.03 mins; MS m/z 356.5 [M+1-1]+; 2minLC_v003

The compounds of the following tabulated intermediates were prepared analogously to Intermediate B1 from the appropriate starting compounds:

TABLE 2

| Int. | Structure | Name | [M + H]+/NMR |
| --- | --- | --- | --- |
| B2 | 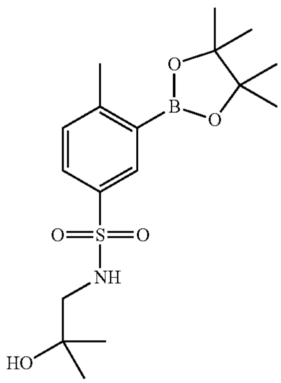 [SMILES: Cc1ccc(S(=O)(=O)NCC(C)(C)O)cc1B1OC(C)(C)C(C)(C)O1] | N-(2-Hydroxy-2-methyl-propyl)-4-methyl-3-(4,4,5,5-tetramethyl[1,3,2]dioxaborolan-2-yl)benzenesulfonamide | LCMS RT 1.20 min. MS m/z 370.3 [M + H]+), Method: 2minLowpHv01 |
| B3 | 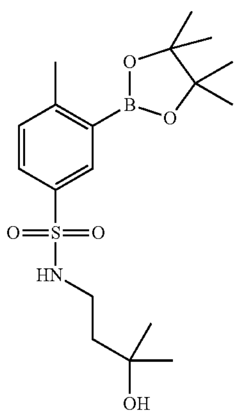 [SMILES: Cc1ccc(S(=O)(=O)NCCC(C)(C)O)cc1B1OC(C)(C)C(C)(C)O1] | N-(3-Hydroxy-3-methylbutyl)-4-methyl-3-(4,4,5,5-tetramethyl-1,3,2-dioxaborolan-2-yl)benzenesulfonamide | LCMS: Rt 1.10 mins; MS m/z 384.5 [M + H]+; Method 2minLC_v003 |
| B4 | 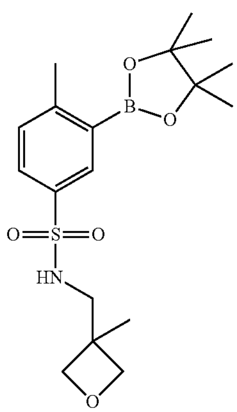 [SMILES: Cc1ccc(S(=O)(=O)NCC2(C)COC2)cc1B1OC(C)(C)C(C)(C)O1] | 4-Methyl-N-(3-methyl-oxetan-3-ylmethyl)-3-(4,4,5,5)tetramethyl-[1,3,2]dioxaborolan-2-yl)-benzenesulfonamide | LCMS: Rt 1.22 mins; MS m/z 382.6 [M + H]+; Method 2minLC_v003 |
| B5 | 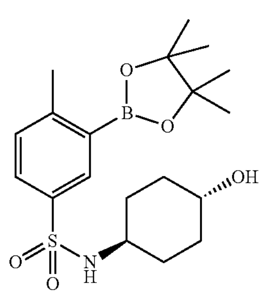 [SMILES: Cc1ccc(S(=O)(=O)N[C@H]2CC[C@H](O)CC2)cc1B1OC(C)(C)C(C)(C)O1] | Trans N-((1r,4r)-4-Hydroxycyclohexyl)-4-methyl-3-(4,4,5,5-tetramethyl-1,3,2-dioxaborolan-2-yl)benzenesulfonamide | LCMS :Rt 1.14 mins; MS m/z 396.3 [M + H]+; Method 2minLC_v003 |

Intermediate C1

2-Chloro-6-(1,3-di methyl-1H-pyrazol-4-yl)-pyrazine

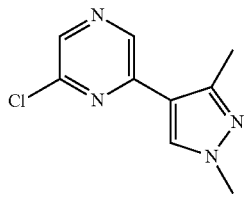

Sodium carbonate (33 ml of a 2M solution, 67 mmol) was added to a mixture of 2-bromo-6-chloropyrazine (4.8 g, 25 mmol), 1,3-dimethyl-4-(4,4,5,5-tetramethyl-1,3,2-dioxaborolan-2-yl)-1H-pyrazole (5.0 g, 22.3 mmol) and PdCl$_2$(PPh$_3$)$_2$ (0.79 g, 67 mmol) in DME (80 ml). The mixture was de-gassed several times under nitrogen then heated with stirring at 70° C. for 3 h. The solvent was removed in vacuo and the residue was diluted with brine and extracted several times with EtOAc. The combined organic extract was separated, dried (MgSO$_4$) and the solvent concentrated in vacuo whereupon the product precipitated (2.21 g, 46%). The solid was collected by filtration and washed with diethyl ether-hexane.

LC-MS: Rt 0.90 mins; MS m/z 209.4 [M+H]+; Method 2minLowpH_v01

1H NMR (400 MHz, CDCl3) δ 8.64 (1H, s), 8.43 (1H, s), 7.92 (1H, s), 3.92 (3H, s), 2.57 (3H, s).

Intermediate C2

4-{2-[4-(6-Bromo-pyrazin-2-yl)-3-methyl-pyrazol-1-yl]-ethyl}-morpholine

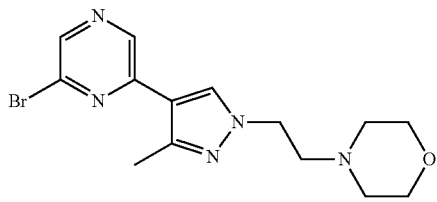 [SMILES: Cc1nn(CCN2CCOCC2)cc1-c1cncc(Br)n1]

Step 1: 4-(2-(3-methyl-4-(4,4,5,5-tetramethyl-1,3,2-dioxaborolan-2-yl)-1H-pyrazol-1-yl)ethyl)morpholine To a solution of 3-methyl-4-(4,4,5,5-tetramethyl-1,3,2-dioxaborolan-2-yl)-1H-pyrazole (300 mg, 1.442 mmol) in MeCN (10 ml) was added cesium carbonate (1.4 g, 4.33 mmol) followed by 4-(2-chloroethyl)morpholine (402 mg, 2.163 mmol) and the reaction was heated at reflux for 5 hours followed by stirring at RT for 18 h. The reaction was filtered under reduced pressure to remove cesium carbonate. The filtrate was concentrated under reduced pressure. The product mixture was purified by flash chromatography on silica gel (24 g) using ISCO combiflash (GPE-15) eluting with DCM/Methanol gradient (0-15%) to give the title compound and it's regioisomer.

LCMS: RT 0.70 mins; MS m/z 323.6 [M+H]+; Method 2minLowpHv01

Step 2: 4-{2-[4-(6-Bromo-pyrazin-2-yl)-3-methyl-pyrazol-1-yl]-ethyl}-morpholine

To a solution of 4-(2-(3-methyl-4-(4,4,5,5-tetramethyl-1,3,2-dioxaborolan-2-yl)-1H-pyrazol-1-yl)ethyl)morpholine and the regioisomer (step 1) (302 mg, 0.799 mmol) in Toluene/EtOH (2:1; 9 ml) was added 2,6-dibromopyrazine (190 mg, 0.799 mmol) followed by Pd(PPh$_3$)$_2$Cl$_2$ (28.0 mg, 0.040 mmol) followed by 2M aqueous sodium carbonate (1.2 ml, 2.396 mmol). The reaction was heated in the microwave at 80° C. for 1 hour. The organic layer of the reaction was isolated and concentrated under reduced pressure to a yellow oil. The product was purified by flash chromatography on silica gel (24 g) using ISCO combiflash (GPE-15) eluting with DCM/MeOH gradient (0-10%) to give two products as a yellow oil which were separated by reverse phase preparative HPLC (Method; 10-35% gradient LowpH). To give the title compound. This was the second compound eluted. The stereochemistry was identified by NOE; the first compound showed a through space interaction between the methyl and methylene whilst the required compound did not.

LCMS: RT 0.61 mins; MS m/z 354.1 [M+H]+; Method 2minLowpH.

1H NMR (400 MHz, d6-DMSO) δ8.88 (1H, s), 8.58 (1H, s), 8.45 (1H, s), 4.20 (2H, t), 3.54 (4H, m), 3.32 (3H, s), 2.72 (2H, t), 2.45 (4H, m).

Intermediate C3

2-Chloro-6-(2,5-dimethyl-2H-pyrazol-3-yl)-pyrazine

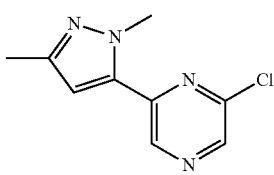

The title compound was prepared from 2-bromo-6-chloropyrazine (4.8 g, 25 mmol) and 1,3-dimethyl-5-(4,4,5,5-tetramethyl-1,3,2-dioxaborolan-2-yl)-1H-pyrazole under analogous conditions to those of Intermediate C1.

LCMS: 0.90 mins; MS m/z 211.3 [M+H]+; Method 2minLowpH 1H NMR (400 MHz, DMSO-d6), δ 9.05 (1H, s), 8.73 (1H, s), 6.84 (1H, s), 4.05 (3H, s), 2.20 (3H, s)

Intermediate D1

3-(6-Chloro-pyrazin-2-yl)-N-(3-hydroxy-3-methyl-butyl)-4-methyl-benzenesulfonamide

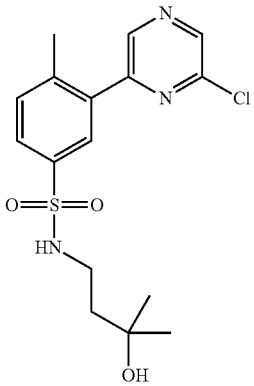 [SMILES: Cc1ccc(S(=O)(=O)NCCC(C)(C)O)cc1-c1cncc(Cl)n1]

A stirred solution of N-(3-hydroxy-3-methylbutyl)-4-methyl-3-(4,4,5,5-tetramethyl-1,3,2-dioxaborolan-2-yl)benzenesulfonamide (Intermediate B3) (1.98 g, 5.17 mmol) and 2-bromo-6-chloropyrazine (1.0 g, 5.17 mmol) in DME (10 ml) and 2M $Na_2CO_3$ (7.8 ml, 15.5 mmol) was de-gassed several times under nitrogen before addition of $PdCl_2$(dppf) . $CH_2Cl_2$ adduct. (0.211 g, 0.26 mmol). The mixture was de-gassed again then heated at 80° C. After 3 h the solvent was removed and the residue was partitioned between EtOAc and water. The organic extract was removed, dried over $MgSO_4$ and the solvent removed to give a brown residue. Chromatography on silica, eluting with EtOAc, gave the product as a colourless gum (1.401 g, 73%)

LCMS: RT 0.95 mins; MS m/z 370.4 [2M+H]+; Method 2minLC_v003.olp

1H NMR (400 MHz, d6-DMSO) 58.96 (1H, s), 8.86 (1H, s), 7.90 (1H, s), 7.82 (1H, s), 7.63 (1H, d), 7.99 (1H, br t), 4.28 (1H, s), 2.83 (2H, m), 2.45 (3H, s), 1.50 (2H, m), 1.00 (6H, s)

Intermediate D2

Trans 3-(6-Chloro-pyrazin-2-yl)-N-(4-hydroxy-cyclohexyl)-4-methyl-benzenesulfonamide

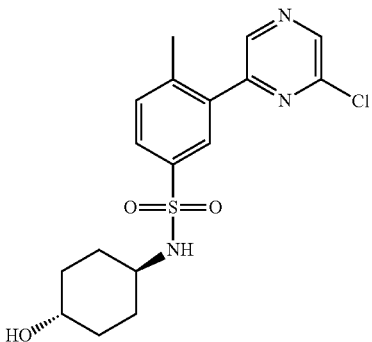 [SMILES: Cc1ccc(S(=O)(=O)N[C@H]2CC[C@H](O)CC2)cc1-c1cncc(Cl)n1]

The title compound was prepared from N-(3-hydroxy-3-methylbutyl)-4-methyl-3-(4,4,5,5-tetramethyl-1,3,2-dioxaborolan-2-yl)benzenesulfonamide (Intermediate B5) and 2-bromo-6-chloropyrazine analogously to Intermediate D1.

LCMS: Rt 1.13 mins; MS m/z 396.3 [M+H]+; Method 2minLC_v003.olp

Pharmaceutical Use and Assay

The compounds of the present invention and their pharmaceutically acceptable salts may be useful as pharmaceuticals. In particular, the compounds are suitable PI 3-kinase gamma isoform selective inhibitors and may be tested in the following assays.

Kinase Glo Luminescent Kinase Assay (Kglo) for PI 3-Kinase Alpha (A), Pb 3-Kinase Beta (B), Vps34 (C), PI 4-Kinase Beta (D)

The luminescence-based ATP detection reagent Kinase-Glo was obtained from Promega, (Cat. No. V6714, Lot No. 236161) through Catalys, Wallisellen, Switzerland. L-alpha-phosphatidylinositol (PI, liver, bovine) was obtained from Avanti Polar Lipid (Cat. No. 840042C, Lot#LPI-274), Phosphatidylinositol-4,5-bisphosphate (PIP(4,5)2) was also obtained from Avanti Polar Lipid (Cat. No. 840046X). L-α-Phosphatidylserine (PS) was obtained from Avanti Polar Lipid (Cat. No. 840032C), n-Octylglucoside from Avanti Polar Lipid (Cat. No. 10634425001). Luminescence is a well established readout to determine ATP concentrations and can thus be used to follow the activity of many kinases regardless of their substrate. The Kinase Glo Luminescent Kinase Assay (Promega, Madison/WI, USA) is a homogeneous HTS method of measuring kinase activity by quantifying the amount of ATP remaining in solution following a kinase reaction.

50 nL of compound dilutions were dispensed onto black 384-well low volume Non Binding Styrene (NBS) plates (Costar Cat. No. NBS#3676). L-α-phosphatidylinositol (PI), provided as 10 mg/ml solution in methanol, was transferred into a glass tube and dried under a nitrogen beam. It was then resuspended in 3% OctylGlucoside (1-O-n-octyl-beta-D-glucopyranoside) by vortexing and stored at 4° C. 5 µL of a mix of PI/OctylGlucoside with the PI 3-kinase alpha and PI 3-kinase beta subtypes, or Vps34 or PI 4-kinase beta were added. Kinase reactions were started by the addition of 5 µl of an ATP-mix containing in a final volume 10 µL 10 mM TRIS-HCl pH 7.5, 3 mM $MgCl_2$, 50 mM NaCl, 0.05% CHAPS, 1 mM DTT and 1 µM ATP at room temperature. Reactions were stopped with 10 µl of KinaseGlo and plates were read 10 mins later in a Synergy2 reader using an integration time of 0.1 seconds per well. 2.5 µM of NVP-BGT226 (1-(3-(trifluoromethyl)-4-(piperazin-1-yl)phenyl)-8-(6-methoxypyridin-3-yl)-3-methyl-1H-imidazo[4,5-c] quinolin-2(3H)-one) was added to the assay plates to generate the 100% inhibition of the kinase reaction, and the 0% inhibition was given by the solvent vehicle (90% DMSO in water). (1-(3-(trifluoromethyl)-4-(piperazin-1-yl)phenyl)-8-(6-methoxypyridin-3-yl)-3-methyl-1H-imidazo[4,5-c] quinolin-2(3H)-one) was used as a reference compound and included in all assay plates in the form of 16 dilution points in duplicate.

$IC_{50}$ values of the percentage inhibition of each compound at 8 concentrations (10, 3.0, 1.0, 0.3, 0.1, 0.030, 0.010 and 0.003 µM) n=2 were derived by fitting a sigmoidal dose-response curve to a plot of assay readout over inhibitor concentration as described. All fits were performed with the program XLfit4 (ID Business Solutions, Guildford, UK).

TR-FRET Adapta Assay for PI 3-Kinase Gamma (E), PI 3-Kinase Delta (F)

The TR-FRET Adapta™ Universal Kinase Assay Kit was purchased from Invitrogen Corporation (Carlsbad/CA, USA) (Cat. No. PV5099). The kit contains the following reagents: Adapta Eu-anti-ADP Antibody (Europium labeled anti-ADP antibody in HEPES buffered saline, Cat. No. PV5097), Alexa Fluor® 647-labeled ADP tracer (Alexa Fluor® 647-labeled ADP tracer in HEPES buffered saline, Cat. No. PV5098), TR-FRET dilution buffer pH 7.5 (Cat. No. PV3574). PIK3CD substrate phosphatidylinositol (PI) was obtained from Invitrogen (vesicles consisting of 2 mM phosphatidylinositol (PI) in 50 mM HEPES pH7.5; Cat. No. PV5371). PIK3CG substrate phosphatidylinositol-4,5-bisphosphate (PIP(4,5)2 was obtained from Invitrogen (PIP2: PS large unilamellar vesicles consisting of 1 mM PIP2: 19 mM PS in 50 mM HEPES pH7.5, 3 mM $MgCl_2$, 1 mM EGTA; Cat. No. PV5100).

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor. TR-FRET assays for protein kinases use a long-lifetime lanthanide Terbium or Europium chelates as the donor species which overcome interference from compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds. The Adapta™ assay can be divided into two phases: a kinase reaction phase and an ADP detection phase. In the kinase reaction phase, all kinase reaction components are added to the well and the reaction is allowed to incubate for a set period of time specific for each kinase. After the reaction, a detection solution of Eu-labeled anti-ADP antibody, Alexa Fluor® 647-labeled ADP tracer, and EDTA (to stop the kinase reaction) are added to the assay well. ADP formed by the kinase reaction will displace the Alexa Fluor® 647-labeled ADP tracer from the antibody, resulting in a decrease in TR-FRET signal. In the presence of an inhibitor, the amount of ADP formed by the kinase reaction is reduced, and the resulting intact antibodytracer interaction maintains a high TR-FRET signal. In the Adapta™ assay, the donor (Europium-anti-ADP antibody) is excited at 340 nm and will transfer its energy to the acceptor (Alexa Fluor® 647-labeled ADP tracer). The emission from the Alexa Fluor® 647 can be monitored with a filter centered at 665 nm because it is located between the emission peaks of the donor, which is measured at 615/620 nm. 50 nL of compound dilutions were dispensed onto white 384-well small volume polystyrene plate. Then 5 µL of either PI 3-kinase gamma or PI 3-kinase delta and lipid substrate (P1 or PIP2:PS) followed by 5 µL of ATP (final assay volume 10 µL) are incubated at RT. The standard reaction buffer for the Adapta™ TR-FRET assay contained 10 mM Tris-HCl pH 7.5, 3 mM $MgCl_2$, 50 mM NaCl, 1 mM DTT, 0.05% CHAPS ((3-[(3-cholamidopropyl)dimethylammonio]-1-propanesulfonate). Reactions were stopped with 5 µL of a mixture of EDTA containing the Eu-labeled anti-ADP antibody and the Alexa Fluor® 647-labeled ADP tracer in TR-FRET dilution buffer. Plates are read 15 to 60 mins later in a Synergy2 reader using an integration time of 0.4 seconds and a delay of 0.05 seconds. Control for the 100% inhibition of the kinase reaction was performed by replacing the PI 3-kinase by the standard reaction buffer. The control for the 0% inhibition was given by the solvent vehicle of the compounds (90% DMSO in $H_2O$). The standard compound 1-(3-(trifluoromethyl)-4-(piperazin-1-yl)phenyl)-8-(6-methoxypyridin-3-yl)-3-methyl-1H-imidazo[4,5-c]quinolin-2(3H)-one (NVP-BGT226) was used as a reference compound and included in all assay plates in the form of 16 dilution points in duplicate.

Data are analyzed using Excel fit software or Graphpad Prism. $IC_{50}$ values were derived by fitting a sigmoidal dose-response curve to a plot of assay readout over inhibitor concentration. All fits were performed with the program XLfit4 (ID Business Solutions, Guildford, UK). Determination of $IC_{50}$ values of the percentage inhibition of each compound at 8 concentrations (usually 10, 3.0, 1.0, 0.3, 0.1, 0.030, 0.010 and 0.003 µM) n were derived by fitting a sigmoidal dose-response curve to a plot of assay readout over inhibitor concentration. All fits were performed with the program XLfit4 (ID Business Solutions, Guildford, UK).

Lanthascreen™ Kinase Binding Assay for mTOR (G)

Binding Assays are based on the binding and displacement of an Alexa Fluor® 647-labeled, ATP-competitive kinase inhibitors to the kinase of interest. Invitrogen's "Kinase Tracers" have been developed to address a wide range of kinase targets and are based on ATP-competitive kinase inhibitors, making them suitable for detection of any compounds that bind to the ATP site or to an allosteric site altering the conformation of the ATP site.

In the Lanthascreen™ kinase binding assay, the donor ($Eu^{3+}$-anti-GST (glutathione 5-transferase) antibody) is excited at 340 nm and will transfer its energy to the acceptor (Alexa Fluor® 647-labeled ATP-competitive kinase inhibitor=Tracer-314). The emission from the Tracer-314 (Alexa Fluor® 647 inhibitor) can be monitored with a filter centered at 665 nm because it is located between the emission peaks of the donor, which is measured at 615/620 nm. The binding of both, the Tracer-314 and $Eu^{3+}$-anti-GST antibody, to the kinase results in a high degree of FRET from the $Eu^{3+}$-donor fluorophore to the Alexa-Fluor® 647-acceptor fluorophore on the Tracer-314. Binding of an inhibitor to the kinase competes for binding with the tracer, resulting in a loss of FRET.

50 nL of compound dilutions were dispensed onto white 384-well small volume polystyrene plate. Then 5 µL of GST-mTOR and Europium-anti-GST antibody followed by 5 µL of tracer-314 (final assay volume 10 µL) are incubated at RT. The standard reaction buffer for the Lanthascreen™ kinase binding assay contained 50 mM HEPES pH 7.5, 5 mM MgCl2, 1 mM EGTA, 0.01% Pluronic F-127. Plates are read 60 mins later in a Synergy2 reader using an integration time of 0.2 microseconds and a delay of 0.1 microseconds.

To calculate the emission ratio, the signal emitted at 665 nm from the acceptor (Alexa Fluor® 647-labeled Tracer-314) is divided by the signal emitted at 620 nm from the donor ($Eu^{3+}$ anti-GST antibody).

Control for the 0% inhibition was given by the solvent vehicle of the compounds (90% DMSO in $H_2O$). Control for the relative 100% inhibition was performed by adding 10 µM in the mix containing GST-mTOR and Europium anti-GST antibody. An additional control for the absolute 0% inhibition is given by $Eu^{3+}$ anti-GST antibody without GST-mTOR. Standard compounds for the lipid kinase panel profiling were used as a reference and included in all assay plates in the form of 8 dilution points.

Cellular Assays for PI 3-Kinase Alpha (H), Beta (I) and Delta (J)

AlphaScreen (Amplified Luminescent Proximity Homogeneous Assay, ALPHA, Perkin Elmer) is a non-radioactive bead-based proximity assay technology to study biomolecular interactions in a homogenous microtiter plate format. The brand name SureFire denotes AlphaScreen assays that are adapted to quantify the phosphorylation of endogenous cellular proteins in cell lysates, by using matched antibody pairs, which consist of an anti-phospho-kinase and an anti-kinase antibody. The assay allows characterization of kinase signaling in cells as well as measurement of kinase inhibitor effects.

Rat-1 cell lines stably overexpressing activated PI 3-kinase class I isoforms Rat-1 pBABEpuro Myr-HA-hp110 delta clone 5 (Rat-1_PI3Kdelta) and Rat-1 pBABEpuro Myr-HA-hp110 alpha clone 6 (Rat-1_PI3Kalpha) and Rat-1 pBABEpuro Myr-HA-hp110 beta (Rat-1_PI3beta) were cultivated in complete growth medium (DMEM high glucose, 10% (v/v) fetal bovine serum, 1% (v/v) MEM NEAA, 10 mM HEPES, 2 mM L-glutamine, puromycin (10 μg/mL for Rat-1_PI3Kdelta and Rat-1_PI3Kalpha, 4 ug/mL for Rat-1_PI3beta), 1% (v/v) Pen/Strep) to 90% confluency at 37° C./5% $CO_2$/90% humidity in a humidified $CO_2$ incubator and were split twice a week. The following materials were used for p-AKT(S473) detection in Rat-1 cell lysates: Dulbecco's modified Eagle's medium (DMEM) high glucose (Gibco Invitrogen, Basel, Switzerland, Cat. No. 41965), heat inactivated fetal bovine serum, qualified (HI FBS; Gibco Invitrogen, Basel, Switzerland, Lot. No. 16140), MEM non essential amino acids (NEAA; Gibco Invitrogen, Basel, Switzerland, Cat. No. 11140), HEPES (Gibco Invitrogen, Basel, Switzerland, Cat. No. 15630), penicillin/streptomycin (Pen/Strep, 100×; Gibco Invitrogen, Basel, Switzerland, Cat. No. 15140-122), L-glutamine (Gibco Invitrogen, Basel, Switzerland, Cat. No. 25030), puromycin (Sigma Aldrich, Buchs, Switzerland, Cat. No. P9620), DMSO (MERCK, Dietikon, Switzerland, Cat. No. 8.02912.2500), $H_2O$, MilliQ-$H_2O$ unless otherwise stated (MILLIPORE QGARDOOR1, Millipore, Zug, Switzerland), bovine serum albumine (BSA; Sigma Aldrich, Buchs, Switzerland Cat. No. A8412), SureFire p-Akt 1/2 (Ser473) Assay Kit (Perkin Elmer, Schwerzenbach, Switzerland, Cat. No. TGRAS50K).

The p-Akt (S473) SureFire assay measures the phosphorylation of endogenous cellular Akt 1/2 at Ser473 in cell lysates. Using Rat-1 cells stably expressing myr-HA-tagged versions of the human PI3Kdelta, PI3Kalpha, or PI3Kbeta p110 catalytic subunit isoforms, the assay was developed as a two-plate protocol in a 384-well format.

For compound testing, the cells were seeded at a density of 4000 (Rat-1_PI3Kdelta), 7500 (Rat-1_PI3Kalpha), or 6200 (Rat-1_PI3Kbeta) cells in 20 μl complete growth medium into cell culture treated 384-well plates and were grown at 37° C./5% $CO_2$/90% humidity for 24 h. Shortly before compound transfer, the complete medium was removed, 30 μl assay buffer (DMEM high glucose, 1×MEM NEAA, 10 mM HEPES, 2 mM L-glutamine, 0.1% (w/v) BSA) was added and 10 μl of the compound predilutions were transferred to the cells. After treatment with compound for 1 h, the cells were lysed by the addition of 20 μl lysis buffer supplemented with 0.24% (w/v) BSA. Detection of p-AKT (Ser473) was performed with the SureFire p-Akt 1/2 (Ser473) Assay Kit according to the manufacturer's instructions using 5 ul of cell lysate in a total detection volume of 12 μl.

$IC_{50}$ values of the percentage inhibition of each compound at 8 concentrations (usually 10, 3.0, 1.0, 0.3, 0.1, 0.030, 0.010 and 0.003 μM) n=2 were derived by fitting a sigmoidal dose-response curve to a plot of assay readout over inhibitor concentration as described. All fits were performed with the program XLfit4 (ID Business Solutions, Guildford, UK).

Cellular U937 AKT Assay for PI 3-Kinase Gamma (K)

The U937 monocyte cell line is maintained in a basal medium of RPMI 1640 supplemented with 10% heat inactivated FCS, 100 U/ml Penicillin, 100 ug/ml streptomycin and 2 mM L-glutamine (Invitrogen). U937 suspension culture is maintained by seeding cells at a density of 0.125×106 cells per ml in fresh medium every three or four days. Cells are incubated at 37° C., 5% CO2. Three or four days prior to assay, cells are seeded at a density of 0.25×106 cells per ml in a total volume of 40 ml in a T162 culture flask.

Before beginning the cell manipulations described below, the MSD (Meso Scale Discovery) assay plate is blocked by addition of 150 ul/well blocking buffer supplied and incubated with shaking for a minimum of one hour at room temperature. All steps of the assay must be performed quickly, with accurately timed incubation periods and observing temperature controls where indicated.

Cells seeded at 0.25×106/ml 3 or 4 days prior to the assay are aspirated, transferred to a 50 ml falcon tube, counted and centrifuged for eight minutes at 300 g at room temperature. Supernatant is aspirated, the cell pellet resuspended and washed once in HBSS (Hank's Balanced Salt Solution) by centrifugation for eight minutes at 300 g at room temperature. The cell pellet is resuspended in HBSS to a concentration of 4×106 per ml, and 100 μL of cell suspension added to each well of a flat-bottomed 96-well tissue culture plate. Assay plates are incubated for 1.5 hours at 37° C., 5% $CO_2$ to allow background AKT phosphorylation to reduce before the compound stimulation step.

A 5 mM stock concentration of compound is prepared in 100% DMSO; from this a 1 in 125 dilution is made in HBSS giving a top compound concentration of 40 μM, 0.8% DMSO. Compound titrations are prepared in a fresh flat-bottomed, 96-well plate, by 10-fold serial dilution of 40 uM into HBSS 0.8% DMSO; pipette tips are replaced after each dilution is made. Compound concentrations at this stage are 4-times the final concentration required in the assay plate. Cells are stimulated with compound or HBSS 0.8% DMSO by direct transfer of 50 ul/well from the compound dilution plate. The assay plate containing compound-treated cells is then incubated for 30 minutes at 37° C. A standard plate layout is used for all experiments.

Compound-treated cells, in addition to positive control wells ("max MIP1α"), are stimulated with 50 μL per well of 40 ng/ml MIP1α (R&D Systems catalogue number 270-LD, lyophilized stock reconstituted to 50 μg/ml with PBS 0.1% BSA). Negative control wells ("min HBSS"), are stimulated with 50 μl/well of HBSS in the absence of MIP1α. Final compound concentrations are now diluted 4-fold giving a top concentration of 10 μM; where added, the final concentration of MIP1α is 10 ng/ml. Cells are incubated with MIP1α for 3 minutes, at 37° C., 5% CO2. After the three minute stimulation period, the assay plate is kept ice cold at all times. Assay plates are centrifuged for 2 minutes at 300 g, 4° C. and supernatant is removed by gently inverting, and then blotting the plate on tissue. Cells are then washed by gentle addition of 150 μL/well of ice cold HBSS and centrifugation at 300 g, for 5 minutes at 4° C. Supernatant is aspirated and the plate blotted as described above. The plate is placed on ice and cells are immediately treated with 35 μL per well of ice cold lysis buffer, prepared according to the kit instructions (per assay plate, to 5 ml of Tris lysis buffer add 100 μl of 50× protease inhibitor solution and 50 μl of each 100× phosphatase inhibitor solutions I and II). Plates are incubated on ice for 20 minutes before centrifugation at 841 g for 5 minutes, 4° C.

Block buffer is aspirated from the MSD plate, and the plate washed four times with 300 µl/well Tris wash buffer. 25 µL of cell lysate is then transferred from the assay plate to the washed MSD plate which is sealed and incubated at room temperature for one hour with shaking. The plate is washed four times with 300 µL per well of Tris wash buffer before addition of 25 µL per well of sulfo-tag anti-total AKT/pAKT detection antibody (60 µl of 50× antibody stock is diluted in 1ml block buffer mixed with 2 ml wash buffer) and incubated at room temperature for one hour with shaking. The plate is washed four times with 300 µl per well of Tris wash buffer and 150 µl per well of Read buffer is added, taking care to avoid the introduction of bubbles. The plate is immediately read using an MSD SECTOR Imager 6000. Results are exported in Excel and the percentage of phosphorylated AKT is calculated using the equation: % Phosphoprotein=((2*Phospho signal)/(Phospho signal+Total signal))*100. Compound-mediated inhibition of AKT phosphorylation is analysed using Prizm V Graphpad software.

Whole Blood Neutrophil Shape Change Assay (L)

A flow cytometry based method used to measure the inhibition of IL-8 (interleukin-8)-induced neutrophil shape change in human whole blood.

Reagents, Material & Equipment
   Sterile Distilled Water, Baxter # UKF117
   10× CellFIX solution, BECTON DICKINSON Biosciences #340181
   IL-8, R&D Systems #208-IL
   DMSO, Hybri-Max, Sigma-Aldrich # D2650
   Dulbecco's Phosphate Buffered Saline 1× HCaCL$_2$, MgCL$_2$, gibco by life technologies #14040
   Albumin Solution from Bovine Serum (30%), Sigma Aldrich # A9576-50 ml
   Ammonium Chloride NH$_4$CL, Sigma Aldrich # A0171
   Potassium Bicarbonate KHCO$_3$, Sigma Aldrich # P9144
   K2 EDTA Vacutainers, Becton Dickinson Vacutainer®#367525
   96-well Polypropylene deep-well plates, VWR # PORV219009
   96 well Plates, V-bottom with lid, Costar #3894
   96 well Polypropylene Plates, Round Bottom, Greiner #650261 (for HIGH THROUGHPUT SAMPLER FACS)
   120 µl pre-sterilized Biohit Filter Tips, Biohit #790101F
   350 µl pre-sterilized Biohit Tips, Biohit #790350
   1200 µl pre-sterilized Biohit Tips, Biohit #791202
   Biohit e1200 Electronic 8-channel Pipette
   Biohit e120 Electronic 8-channel Pipette
   Eppendorf Research Plus 100-1000 µl Pipette
   Eppendorf Research Plus 20-200 µl Pipette
   Becton Dickinson Biosciences FACS Canto 11 Flow Cytometer with HIGH THROUGHPUT SAMPLER IL-8 was made up to 2 µM stocks in 0.1% bovine serum albumin/PBS and stored at −80° C. On the day IL-8 was diluted in PBS (phosphate buffered saline) 10 minutes before use. IL-8 was used at final concentration of 2 nM and a concentration range from 0.003 to 200 nM for the donor dose response curve.

Assay fixative solution was prepared fresh each day from 10× concentrated CellFIX™ solution diluted 1:10 in sterile distilled water and then 1:4 with PBS. Assay fixative solution was kept on ice prior to use.

A 10× lysis buffer was prepared in advance by dissolving 20.75 g NR$_4$Cl and 2.5 g KHCO$_3$ in 250 ml sterile H$_2$O. This 10× lysis buffer was filtered under sterile conditions and stored for up to two weeks at 4° C. On the day a 1× lysis solution was prepared with sterile distilled H$_2$O and kept on ice prior to use.

The test compounds were prepared as 10 mM stock solutions in 100% DMSO and were stored at 4° C. Once in use for an assay 10 mM stock compounds were thawed and stored at RT protected from light. Compound dilutions were prepared fresh on the day. The first series of dilutions in 100% DMSO were done first thing in the morning. Only once blood had been collected and arrived in laboratory was the next set of dilutions into PBS carried out (1:10 PBS, 10% DMSO). This limited the exposure of diluted compound to plastic and made sure the exposure timing was consistent between assays. Compounds were added to the deep 96 well plates at 10× the final desired concentration (with addition of blood final [DMSO]=1%).

Table 3 illustrates the compound dilution series used in human whole blood neutrophil shape change assay.

TABLE 3

| 100% DMSO Serial Dil'n 1 in 4 | 10% DMSO 1 in 10 PBS | 1% DMSO Assay Plate | $_{example}$Well ID* |
|---|---|---|---|
| 10000 µM | 1000 µM | 100 µM | B2; CPD + IL-8 |
| 2500 | 250 | 25 | B3; CPD + IL-8 |
| 625 | 62.5 | 6.25 | B4; CPD + IL-8 |
| 156.25 | 15.62 | 1.56 | B5; CPD + IL-8 |
| 39.0625 | 3.9 | 0.39 | B6; CPD + IL-8 |
| 9.765625 | 0.97 | 0.097 | B7; CPD + IL-8 |
| 2.441406 | 0.24 | 0.024 | B8; CPD + IL-8 |
| 0.610352 | 0.06 | 0.006 | B9; CPD + IL-8 |
| 100% DMSO | 10% DMSO | 1% DMSO | B10; +IL-8 |
| 100% DMSO | 10% DMSO | 1% DMSO | B11; +PBS |

On the day of running the assay, assay fixative buffer and 1× lysis solutions were prepared and stored on ice. Compound dilutions in 100% DMSO were prepared as described previously. Human whole blood was collected in K2 EDTA Vacutainers. Once blood was in the laboratory, compound dilutions into PBS were carried out as described previously and depicted in Table 1. 10 µl of 10× final compound concentration was added to appropriate wells of a deep 96-well plate except controls where 10 µl of 10% DMSO was added in place of compound, as outlined in the dilution series in Table 1. The outer wells of the deep well assay plate were filled with 1200 µl of sterile distilled H$_2$O in an effort to limit edge effects (rows A1-H1, A1-A12, A12-H12). An IL-8 dose response was determined for each blood donor examined, to monitor the donor response to IL-8. At this step in assay preparation for the IL-8 dose response samples 10 µl of PBS was added to designated wells. In addition the assay window without DMSO was also assessed each day. For such samples at this step in assay preparation 10 µl of PBS was added in the place of 10% DMSO.

80 µl of whole blood was added to compound/10% DMSO/PBS and mixed once gently upon addition. Lids were placed on the 96 well plates and samples were incubated for 15 minutes at 37° C. in a water-bath.

Following the compound pre-incubation 10× final IL-8 was added to appropriate wells (10 µl of 20 nM working stock IL-8, final IL-8 concentration in blood=2 nM) and 10 µl of PBS was added to the un-stimulated controls. 10× final dose response range IL-8 was also added to designated wells (final concentration range on assay plate was 200 nM to 0.0005 nM, 1:5 serial dilution in PBS). The IL-8 and PBS were added to appropriate wells across all assay plates in the same sequence as the blood to compound addition. Once added to all assay plates, samples were mixed quickly once to ensure even distribution of IL-8. Samples were incubated for 5 minutes at 37° C. in a water-bath. Following the incubation sample plates were transferred to ice where 250 µl of chilled Assay Fixative Buffer was added promptly to all wells.

Samples were incubated on ice for 7 minutes (no mixing). Following fixation 1.2 ml of 1x Lysis Solution was then added promptly to each well. Once added samples were mixed once and incubated on ice for 30 minutes to achieve uniform red blood cells lysis. After lysis, 200 µl of sample was transferred to a 96 well microplate on ice. Samples were acquired using the HTS on high throughput mode on a Becton Dickinson FACS Canto II. Granulocytes were identified based on differential side scatter (SSC) and forward scatter (FSC) characteristics. Neutrophils were distinguished from eosinophils using the phycoerythrin channel, as the latter have higher auto-fluorescence.

The mean FSC value for the neutrophil population was taken as measure of cell shape change (the greater the FSC value meant the greater the degree of shape change). Data was presented as % shape change over basal for the IL-8 dose response curve and assay window controls and presented as % inhibition of shape change for compound treated samples.

% Shape Change Above Basal

Subtract the un-stimulated control FSC reading from agonist FSC readings, divide results by the un-stimulated FSC value and multiply by 100 to give % shape change above basal.

% inhibition

% inhibition=(X−Y)/X*100 (FIG. 2. for sample values)

X=IL-8 FSC response minus the un-stimulated control (basal) FSC.

(120,984−86,163=34821=X)

Y=IL-8 FSC response in compound treated samples minus the un-stimulated control (basal) FSC.

(89,841−86,163=3678=Y)

(34821−3678)/34821*100=89% inhibition of shape change

The % inhibition values were plotted on the Y-axis against compound concentration on the x-axis, to give $IC_{50}$ values.

The biochemical assay data for examples 1-13 is provided in the following table:

TABLE 4

| | Biochemical assay data | | | | | | |
|---|---|---|---|---|---|---|---|
| Example | Assay A PI3Kα IC50 (µM) | Assay B PI3Kβ IC50 (µM) | Assay C VPS34 IC50 (µM) | Assay D PI4Kβ IC50 (µM) | Assay E PI3Kγ IC50 (µM) | Assay F PI3Kδ IC50 (µM) | Assay G mTOR IC50 (µM) |
| 1 | 0.19 | 6.16 | 3.07 | >9.1 | 0.022 | 0.20 | 5.25 |
| 2 | 0.05 | 0.71 | 3.45 | >9.775 | 0.019 | 0.06 | 1.18 |
| 3 | 0.08 | 1.45 | 5.30 | >9.55 | 0.048 | 0.07 | 3.85 |
| 4 | 0.06 | 0.68 | 4.30 | >10 | 0.014 | 0.07 | 0.89 |
| 5 | 0.15 | 1.12 | 1.81 | >9.1 | 0.015 | 0.09 | 4.77 |
| 6 | 0.04 | 0.45 | 9.40 | >10 | 0.013 | 0.09 | 0.77 |
| 7 | 0.09 | 0.63 | 4.40 | >9.1 | 0.011 | 0.10 | 6.00 |
| 8 | 0.06 | 0.68 | 4.40 | >9.55 | 0.020 | 0.07 | 1.95 |
| 9 | 0.26 | >9.10 | >9.1 | >9.1 | 0.160 | 0.01 | >9.1 |
| 10 | 0.07 | 8.50 | >10 | >10 | 0.027 | 0.02 | 9.80 |
| 11 | 0.40 | 3.93 | 3.08 | >9.1 | 0.088 | 0.12 | 6.24 |
| 12 | 0.16 | >9.10 | 8.60 | >9.1 | 0.006 | 0.01 | >9.1 |
| 13 | 0.10 | 1.90 | 2.45 | >9.55 | 0.038 | 0.04 | 3.00 |

The cellular assay data and whole blood shape change functional assay data for examples 1-13 is provided in the following table:

TABLE 5

| | Cellular assay data and whole blood shape change data | | | | |
|---|---|---|---|---|---|
| Example | Assay H PI3Kα IC50(µM) | Assay I PI3Kβ IC50(µM) | Assay J PI3Kδ IC50(µM) | Assay K PI3Kγ IC50(µM) | Assay L WBSC IC50(µM) |
| 1 | | | | 0.329 | 1.331 |
| 2 | 0.45 | 0.784 | 0.3665 | 0.066 | 0.266 |
| 3 | 1.02 | 3.18 | 1.37 | 0.080 | 1.075 |
| 4 | 0.293 | 0.833 | 0.285 | 0.054 | 0.548 |
| 5 | 0.838 | 9.42 | 0.54 | 0.038 | 0.179 |
| 6 | 0.709 | 1.05 | 0.515 | 0.022 | 0.374 |
| 7 | | | | 0.061 | 0.212 |
| 8 | | | | 0.096 | 0.625 |
| 9 | 2.48 | 6.98 | 1.68 | 0.599 | 0.598 |
| 10 | 3.09 | 3.83 | 0.771 | 0.121 | 0.663 |
| 11 | 1.7 | >10 | 1.05 | 0.213 | 0.752 |
| 12 | 1.14 | 1.11 | 0.306 | 0.122 | 0.830 |
| 13 | | | | 0.122 | 0.847 |

The invention claimed is:

1. A compound of formula (I),

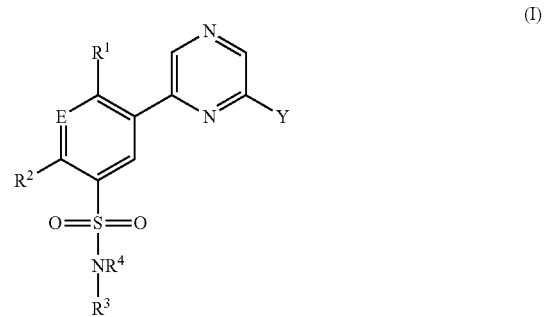

wherein

E is selected from N and $CR^E$;

$R^1$, $R^2$ and $R^E$ are independently selected from H, halogen, $C_{1-4}$ alkyl, $C_{1-4}$ alkoxy, $C_{1-4}$ haloalkyl, $C_{1-4}$ haloalkoxy and $C_{3-6}$ cycloalkyl;

R³ is selected from
(i) $C_{1-4}$ alkyl which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(ii) $C_{1-4}$ alkoxy which is unsubstituted or substituted with 1 to 3 substituents independently selected from hydroxy, $C_{1-4}$ hydroxyalkyl, halogen, $C_{1-4}$ haloalkyl, $C_{1-4}$ alkyl, $C_{1-4}$ alkoxy, oxo, —$NR^{3a}R^{3b}$ and $C_{3-6}$ cycloalkyl, and wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy and $C_{1-4}$ haloalkyl;
(iii) —$C_{3-6}$ cycloalkyl or —O—$C_{3-6}$ cycloalkyl wherein the $C_{3-6}$ cycloalkyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;
(iv) —($C_{0-3}$ alkyl)-$C_{3-6}$ cycloalkyl or —(O—$C_{0-3}$ alkyl)-$C_{3-6}$ cycloalkyl spiro fused to a second $C_{3-6}$ cycloalkyl or $C_{3-6}$ heterocyclyl by one single carbon atom, wherein the $C_{3-6}$ cycloalkyl or $C_{3-6}$ heterocyclyl is unsubstituted or substituted with 1 to 3 substituents independently selected from hydroxy, $C_{1-4}$ hydroxyalkyl, halogen, $C_{1-4}$ alkoxy, $C_{1-4}$ haloalkyl and —($C_{0-3}$ alkyl)-$NR^{3a}R^{3b}$;
(v) —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$; and
(vi) —($C_{0-3}$ alkyl)-$C_{3-6}$ heterocyclyl or —(O—$C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, $C_{1-4}$ alkoxy, hydroxy, $C_{1-4}$ hydroxyalkyl, halogen, $C_{1-4}$ haloalkyl and —($C_{0-3}$ alkyl)-$NR^{3a}R^{3b}$;
$R^{3a}$ and $R^{3b}$ are independently selected from H, $C_{1-4}$ alkyl and $C_{1-4}$ haloalkyl;
$R^4$ is selected from H and $C_{1-4}$ alkyl; or
$R^3$ and $R^4$ together with the nitrogen atom to which they are attached form a $C_{3-6}$ heterocyclyl, which $C_{3-6}$ heterocyclyl is optionally spiro fused to a second $C_{3-6}$ heterocyclyl or a $C_{3-6}$ cycloalkyl by one single carbon atom, and which $C_{3-6}$ heterocyclyl and $C_{3-6}$ cycloalkyl are unsubstituted or substituted with 1 to 3 substituents independently selected from $C_{1-4}$ alkyl, hydroxy, $C_{1-4}$ hydroxyalkyl, halogen, $C_{1-4}$ alkoxy and $C_{1-4}$ haloalkyl; and
Y is a 5-6-membered heteroaryl, which heteroaryl is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, —($C_{0-3}$ alkyl)-$NR^{3a}R^{3b}$, —($C_{0-3}$ alkyl)-$C_{3-6}$ cycloalkyl and —($C_{0-3}$ alkyl)-$C_{3-6}$ heterocyclyl;
or a pharmaceutically acceptable salt thereof.

2. The compound or salt according to claim 1, wherein $R^3$ is selected from
(i) $C_{1-4}$ alkyl substituted with 1 to 3 substituents independently selected from hydroxy, $C_{1-4}$ alkyl, halogen, oxo, and —$NR^{3a}R^{3b}$;
(ii) $C_{1-4}$ alkoxy substituted with 1 to 3 substituents independently selected from hydroxy, halogen and $C_{1-4}$ alkyl;
(iii) —($C_{0-3}$ alkyl)-$C_{3-6}$ cycloalkyl wherein the $C_{3-6}$ cycloalkyl is substituted with 1 to 3 substituents independently selected from hydroxy, $C_{1-4}$ hydroxyalkyl and halogen;
(iv) —($C_{0-3}$ alkyl)-$C_{3-6}$ cycloalkyl spiro fused to a second $C_{3-6}$ cycloalkyl by one single carbon atom, wherein the second $C_{3-6}$ cycloalkyl is substituted with 1 to 3 substituents independently selected from hydroxy and halogen;
(v) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is unsubstituted or substituted with 1 to 3 substituents independently selected from hydroxy, $C_{1-4}$ alkyl and $C_{1-4}$ hydroxyalkyl; and
(vi) —($C_{0-3}$ alkyl)-$C_{3-6}$ heterocyclyl wherein the $C_{3-6}$ heterocyclyl contains at least one heteroatom selected from O and N, and wherein said $C_{3-6}$ heterocyclyl is spiro fused to a second $C_{3-6}$ heterocyclyl or a $C_{3-6}$ cycloalkyl by one single carbon atom, and wherein the $C_{3-6}$ heterocyclyl or $C_{3-6}$ cycloalkyl is unsubstituted or substituted with 1 to 3 substituents independently selected from $C_{1-4}$ alkyl, hydroxy and $C_{1-4}$ hydroxyalkyl;
$R^{3a}$ and $R^{3b}$ are independently selected from H and $C_{1-4}$ alkyl;
$R^4$ is selected from H and $C_{1-4}$alkyl; or
$R^3$ and $R^4$ together with the nitrogen atom to which they are attached form a $C_{3-6}$ heterocyclyl, which $C_{3-6}$ heterocyclyl is unsubstituted or substituted with 1 to 3 substituents independently selected from hydroxy, $C_{1-4}$ hydroxyalkyl and $C_{1-4}$ alkyl.

3. The compound or salt according to claim 1, wherein Y is selected from
thiazolyl,
pyrazolyl,
pyridyl,
triazolyl,
imidazolyl,
oxadiazolyl,
pyrimidinyl,
isoxazolyl,
oxazolyl, and
thienyl;
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy, halogen, $C_{1-4}$ hydroxyalkyl, $C_{1-4}$ alkoxyalkyl, —$NR^{3a}R^{3b}$, —($C_{0-3}$ alkyl)-$C_{3-6}$ cycloalkyl and —($C_{0-3}$ alkyl)-$C_{3-6}$ heterocyclyl.

4. The compound or salt according to claim 1, wherein Y is selected from
thiazol-5-yl,
pyrazol-4-yl,
pyrazol-5-yl,
pyrazol-1-yl, pyrid-4-yl,
pyrid-3-yl,
1,2,4-triazol-1-yl,
1,2,3-triazol-4-yl,
imidazol-1-yl,
1,2,4-oxadiazol-5-yl,
1,3,4-oxadiazol-2-yl,
thien-3-yl,
isoxazol-5-yl, and
pyrimidin-5-yl,
each of which is unsubstituted or substituted with 1 to 3 substituents independently selected from $C_{1-4}$ alkyl, $C_{1-4}$ haloalkyl, $C_{1-4}$alkoxy$C_{1-4}$alkyl, $C_{1-4}$hydroxyalkyl, $C_{1-4}$ alkoxy, $C_{1-4}$ haloalkoxy and —($C_{0-3}$ alkyl)-$C_{3-6}$ cycloalkyl.

5. The compound or salt according to claim 1, wherein Y is selected from
thiazol-5-yl,
pyrazol-4-yl,
pyrazol-5-yl,
pyrazol-1-yl,
pyrid-4-yl,
pyrid-3-yl,
1,2,4-triazol-1-yl,
1,2,3-triazol-4-yl,
imidazol-1-yl,
1,2,4-oxadiazol-5-yl,
isoxazol-5-yl,
pyrimidin-5-yl, and
thien-3-yl,
each of which is unsubstituted or substituted with 1 to 3 substituents independently selected from methyl, ethyl, propyl, isopropyl, cyclopropyl, $CF_3$, hydroxyethyl, methoxyethyl and methoxy.

6. The compound or salt according to claim 1, wherein $R^3$ is selected from propyl, butyl and pentyl substituted by 1 to 3 substituents independently selected from hydroxy, $C_{1-4}$ alkyl, halogen, —$NR^{3a}R^{3b}$, and oxo.

7. The compound or salt according to claim 1, wherein $R^1$ is selected from $C_{1-4}$ alkyl and H; and $R^2$ is selected from H, $C_{1-4}$ alkyl and halogen.

8. The compound according to claim 1 selected from
N-(3-Hydroxy-propyl)-4-methyl-3-[6-(2-methyl-thiazol-5-yl)-pyrazin-2-yl]-benzenesulfonamide;
3-[6-(1,3-Dimethyl-1H-pyrazol-4-yl)-pyrazin-2-yl]-N-(2-hydroxy-2-methyl-propyl)-4-methyl-benzenesulfonamide;
3-[6-(1,3-Dimethyl-1H-pyrazol-4-yl)-pyrazin-2-yl]-N-(3-hydroxy-3-methyl-butyl)-4-methyl-benzenesulfonamide;
3-[6-(1,3-Dimethyl-1H-pyrazol-4-yl)-pyrazin-2-yl]-4-methyl-N-(3-methyl-oxetan-3-ylmethyl)-benzenesulfonamide;
N-((1r,4r)-4-Hydroxycyclohexyl)-4-methyl-3-(6-(2-methylthiazol-5-yl)pyrazin-2-yl)benzenesulfonamide;
3-[6-(1,3-Dimethyl-1H-pyrazol-4-yl)-pyrazin-2-yl]-N-(6-hydroxy-spiro[3.3]hept-2-yl)-4-methyl-benzenesulfonamide;
3-[6-(1,3-Dimethyl-1H-pyrazol-4-yl)-pyrazin-2-yl]-N-(3-hydroxy-cyclobutylmethyl)-4-methyl-benzenesulfonamide;
3-[6-(1,3-Dimethyl-1H-pyrazol-4-yl)-pyrazin-2-yl]-N-(3-hydroxy-2,2-dimethyl-propyl)-4-methyl-benzenesulfonamide;
N-(3-Hydroxy-3-methyl-butyl)-4-methyl-3-{6-[1-(2-morpholin-4-yl-ethyl)-1H-pyrazol-4-yl]-pyrazin-2-yl}-benzenesulfonamide;
N-(3-Hydroxy-3-methyl-butyl)-4-methyl-3-{6-[3-methyl-1-(2-morpholin-4-yl-ethyl)-1H-pyrazol-4-yl]-pyrazin-2-yl}-benzenesulfonamide;
N-(4-Hydroxy-cyclohexyl)-4-methyl-3-(6-pyridin-3-yl-pyrazin-2-yl)-benzenesulfonamide;
N-(4-Hydroxy-cyclohexyl)-4-methyl-3-[6-(5-morpholin-4-ylmethyl-thiophen-3-yl)-pyrazin-2-yl]-benzenesulfonamide; and
3-[6-(2,5-Dimethyl-2H-pyrazol-3-yl)-pyrazin-2-yl]-N-(3-hydroxy-cyclobutylmethyl)-4-methyl-benzenesulfonamide;
or a pharmaceutically acceptable salt thereof.

9. A pharmaceutical composition, comprising:
a therapeutically effective amount of the compound or salt according to claim 1 and one or more pharmaceutically acceptable carriers.

10. A pharmaceutical combination, comprising:
a therapeutically effective amount of the compound or salt according to claim 1 and a second active agent.

11. A method of treating a disorder or disease mediated by the activation of PI 3-kinase gamma isoform, comprising administering to a subject having the disorder or disease a therapeutically effective amount of a compound or salt according to claim 1.

12. The method of claim 11, wherein the disorder or disease is selected from the group consisting of respiratory diseases, allergies, rheumatoid arthritis, osteoarthritis, rheumatic disorders, psoriasis, ulcerative colitis, Crohn's disease, septic shock, proliferative disorders, atherosclerosis, allograft rejection following transplantation, diabetes, stroke, obesity and restenosis.

13. The method of claim 12, wherein the disorder or disease is cancer.

14. A pharmaceutical composition, comprising:
a compound or salt according to claim 1 and one or more pharmaceutically acceptable carriers.

15. A pharmaceutical combination, comprising:
a compound or salt according to claim 1 and a second active agent.

16. A pharmaceutical composition, comprising:
a compound or salt according to claim 8 and one or more pharmaceutically acceptable carriers.

17. A pharmaceutical combination, comprising:
a compound or salt according to claim 8 and a second active agent.

18. A method of treating a disorder or disease mediated by the activation of PI 3-kinase gamma isoform, comprising administering to a subject having the disorder or disease a therapeutically effective amount of a compound or salt according to claim 8.

19. The method of claim 18, wherein the disorder or disease is selected from the group consisting of respiratory diseases, allergies, rheumatoid arthritis, osteoarthritis, rheumatic disorders, psoriasis, ulcerative colitis, Crohn's disease, septic shock, proliferative disorders, atherosclerosis, allograft rejection following transplantation, diabetes, stroke, obesity and restenosis.

20. The method of claim 19, wherein the disorder or disease is cancer.

* * * * *